(12) United States Patent
Konofagou et al.

(10) Patent No.: US 6,270,459 B1
(45) Date of Patent: Aug. 7, 2001

(54) METHOD FOR ESTIMATING AND IMAGING OF TRANSVERSE DISPLACEMENTS, TRANSVERSE STRAINS AND STRAIN RATIOS

(75) Inventors: Elisa Konofagou; Jonathan Ophir, both of Houston, TX (US)

(73) Assignee: The Board of Regents of the University of Texas System, Houston, TX (US)

( * ) Notice: Subject to any disclaimer, the term of this patent is extended or adjusted under 35 U.S.C. 154(b) by 0 days.

(21) Appl. No.: 09/320,353

(22) Filed: May 26, 1999

Related U.S. Application Data

(60) Provisional application No. 60/086,767, filed on May 26, 1998.

(51) Int. Cl.[7] ................................................ A61B 8/00

(52) U.S. Cl. ................................................ 600/449

(58) Field of Search .................................. 600/443, 449, 600/438, 437, 442; 73/573, 597, 789

(56) References Cited

U.S. PATENT DOCUMENTS

| | | | |
|---|---|---|---|
| 5,000,184 | | 3/1991 | Bonnefous . |
| 5,291,892 | * | 3/1994 | O'Donnell ........................ 600/455 |
| 5,474,070 | * | 12/1995 | Ophir et al. ........................ 600/437 |
| 5,495,771 | * | 3/1996 | Sumi et al. ........................ 73/789 |
| 5,524,636 | * | 6/1996 | Sarvazyon et al. ................ 600/587 |
| 5,692,520 | | 12/1997 | Lavoisier . |
| 5,701,898 | | 12/1997 | Adam et al. . |
| 5,924,986 | * | 7/1999 | Chandler et al. .................. 600/443 |

OTHER PUBLICATIONS

Alam, S.K., et al.; An Adaptive Strain Estimator for Elastography, *IEEE Trans. Ulstrson., Ferroel, Freq. Cont.*; 45:2, Mar. 1998, 461–472.

Bamber, J.C., et al.; Freehand Elasticity Imaging Using Speckle Decorrelation Rate, *Acoustical Imaging*, 22, 1996, 285–292.

Bendat, J.S., et al.; Random Data, Analysis and Measurement Procedures, John Wiley & Sons, New York, 2nd Edition; 1986, 118–120.

Bohs, L.N., et al.; A Novel Method for Angle Independent Ultrasonic Imaging of Blood Flow and Tissue Motion, *IEEE Trans. Biomed. Eng.*; 38:3, Mar. 1991, 280–286.

Bohs, L.N., et al.; Experimental Velocity Profiles and Volumetric Flow via Two–Dimensional Speckle Tracking, *Ultrasound in Med & Biol.*;21:7, 1995, 885–898.

Bonnefous, O.; Measurement of the Complete (3D) Velocity Vector of Blood Flows, *IEEE Ultrason. Symp*; 1988, 795–799.

Bonnefous, O.; Statistical Analysis and Time Correlation Processes Applied to Velocity Measurement; *IEEE Ultrason, Symp*; 1989, 887–892.

Burckhardt, C.B.; Speckle in Ultrasound B–Mode Scans, *IEEE Trans. on Son. And Ultras*; SU–25:1, Jan. 1978, 1–6.

Cespedes, I., et al.; Reduction of Noise in Elastography, *Ultrasonic Imaging*; 15, 1993, 89–102.

(List continued on next page.)

Primary Examiner—Francis J. Jaworski
(74) Attorney, Agent, or Firm—Duane, Morris & Heckscher LLP

(57) ABSTRACT

The present invention is directed toward a new method that combines interpolation between neighboring A-lines with cross-correlation for high precision estimation of the transverse displacement. Due to this high precision lateral estimation, the method of the present invention can produce quality lateral-elastograms that display the lateral component of the strain tensor. These higher precision lateral displacement estimates also allow a finer correction for the lateral decorrelation that corrupts the axial estimation. The method of the present invention may be employed to divide the lateral-elastogram by the axial-elastogram on a pixel-by-pixel basis, in order to produce a new image that displays the distribution of Poisson's ratios in the tissue.

27 Claims, 15 Drawing Sheets

OTHER PUBLICATIONS

Chaturvedi, P., et al.; 2–D Companding for Noise Reduction in Strain Imaging, *IEEE Trans. of Ultras., Ferroel. and Freq. Cont.*: 45:1, Jan. 1998, 179–191.

Insana, M.F., et al.; E–D companding using Linear Arrays for Improved Strain Imaging, *IEEE Ultrason. Symp*; Oct. 1997, 4 pages.

Chon, N.A., et al.; An Elasticity Microscope. Part I: Methods, *IEEE Trans. of Ultras., Ferroel. and Freq. Cont.*; 44:6, Nov. 1997, 1304–1319.

Dotti, D., et al.; Vectorial Measurement of Blood Velocity by Means of Ultrasound, *Med. Biol. Eng. Comp.*, Mar. 1992, 219–224.

Fung, Y.C.; Connecting incremental shear modulus and Poisson's ratio of lung tissue with morphology and rheology of microstructure, *Biorheology* 26: 279–289; 1989.

Geiman, B.J.; Bohs, L.N.; Anderson M.E.; Czensak, S.P.; Trahey, G.E. 2D vector flow imaging using ensemble tracking: initial results, *Ultras. Imag.* 18: 61–62; 1996.

Hein, I.A.; Multi–directional ultrasonic blood flow measurement with a triple beam lens, *Proc. IEEE Ultrason. Symp.*: 1065–1069; 1993.

Hein, I.A.; O'Brien, W.D. Current Time–domain Methods for assessing tissue motion by analysis from reflected ultrasound echoes—a review. *IEEE Trans on Ultras., Ferroel, and Freq. Control* UFFC–40, No.2, 1993.

Insana M.; Chaturvedi P.; Hall T.; Bilgen, M.; 3D companding using 1.5D arrays for improved strain imaging. *IEEE Ultrason. Symp.*; 1997.

Irons, B; Ahmad, A.; Techniques of finite elements, *Ellis Horwood*, p. 461; 1980.

Jensen, J.A.; Estimation of blood velocities using ultrasound, Cambridge University Press; 1996.

Jurvelin, J.S.; Buschmann, M.D.; Hunziker, E.B.; Optical and mechanical determination of Poisson's ratio of adult bovine humeral articular cartilage. *J. Biomechanics* 30, No.3: 235–241; 1997.

Kallel F.; Proprietes elastiques des tissus mous a partir de l'analyse des changements spatio–temporels dans les signaux ultrasonores. PhD dissertation, Ecole Polytechnique, University of Montreal, Montreal, Quebec, Canada; 1995.

Kallel, F.; Bertrand, M.; Tissue elasticity reconstruction using linear perturbation method. *IEEE Trans. Med. Imag.* 15: 299–313; 1996.

Kallel, F.; Ophir, J.; Three–dimensional tissue motion and its effect on image noise in elastography. *IEEE Trans of Ultras., Ferroel. and Freq. Control* 44:1286–1296; 1997.

Kallel, F.; Varghese, T.; Ophir, J.; Bilgen, M.; The nonstationary strain filter in elastography, Part II: Lateral and elevational decorrelation. *Ultrasound in Med. and Biol.* 23 ( 9): 1357–1369; 1997.

Kallel, F.; Ophir, J.; Elastographic imaging of low contrast elastic modulus distributions in tissue, *IEEE Trans of Ultras., Ferroel. and Freq. Control*; 1997b (in press).

Kallel, F.; Bertrand, M.; Ophir, J.; Fundamental limitations on the contrast–transfer efficiency in elastography: An analytic study. *Ultras. in Med. and Biol.* 22(4): 463–470; 1996.

Kallel, F.; Ophir, J.; A least squares estimator for elastography. *Ultrasonic Imaging*; 1997d (in press).

Kino, G.S.; Acoustic waves: devices, imaging and analog signal processing. Prentice Hall; 1987.

Lai W.M.; Rubin D.; Krempl, E.; Introduction to Continuum Mechanics. Pergamon Press; 1978.

Lubinski, A.M.; Emelianov, S.Y.; Raghavan, K.R.; Yagle, A.E.; Skovoroda, A.R.; O'Donnell, M. Lateral displacement estimation using tissue incompressibility, *IEEE Trans of Ultras., Ferroel. and Freq. Control* 43(2); 1996.

Mridha, M.; Ödman S.; Noninvasive method for assessment of subcutaneous edema, *Med. and Biol. Engineering and Computing* 24: 393–398; 1986.

Ophir, J.; Johnson, W.; Yazdi, Y.; Shattuck, D.; Mehta, D.; Correlation artifacts in speed of sound estimation in scattering media. *Ultras. in Med. and Biol.* 15 (4): 341–353; 1989.

Ophir, J.; Céspedes, I.; Ponnekanti, H.; Yazdi, Y.; Li, X.; Elastography: a quantitative method for imaging the elasticity of biological tissues, *Ultrasonic Imaging* 13: 111–134; 1991.

Ophir, J; Cespedes, I; Garra, B.; Ponnekanti, H; Huang, Y; Maklad, N; Elastography: ultrasonic imaging of tissue strain and elastic modulus in vivo, *European Journal of Ultraound* 3: 49–70;1996.

Ophir, J.; Kallel, F.; Varghese, T.; Bertrand, M.; Céspedes, I.; Ponnekanti, H.; Elastography: A systems approach; *The Int. J. Imag. Sys. Tech.*, John Wiley & Sons, Inc 8: 89–103; 1997.

Ramamurthy, B.S.; Trahey, G.E.; Potential and limitations of angle–independent flow detection algorithms using radio–frequency and detected echo signals, *Ultrasonic imaging* 13: 252–268; 1991.

Rice, J.R.; Cleary, M.P.; Some basic stress diffusion solutions for fluid–saturated elastic porous media with compressible constituents, *Reviews of Geophysics and Space Physics* 14(2): 227–241; 1976.

Saada, A.S.; Elasticity, theory and applications, New York: Pergamon Press: 377–399; 1989.

Sarvazyan, A.P.; Low frequency acoustic properties of biological tissues, *Mechanics of Polymers* 4:691–695; 1975.

Skovoroda, AR; Emelianov, SY; Lubinski, AM; Sarvazyan, A.P.; O'Donnell, M.; Theoretical analysis and verification of ultrasound displacement and strain imaging; *IEEE Trans of Ultras., Ferroel. and Freq. Control* 41(3); 1994.

Skovoroda, A.R.; Emelianov, S.Y.; O'Donnell, M.; Tissue elasticity reconstruction based on ultrasonic displacement and strain images, *IEEE Trans of Ultras., Ferroel. and Freq. Control* 42: 747–765; 1995.

Sumi C.; Suzuki A.; Nakayama K.; Estimation of shear modulus distribution in soft tissue from strain distribution, *IEEE Trans Biomed Eng.* 42: 193–202; 1995.

Trahey, G.E. Allison, J.W. von Ramm, O.T.; Angle independent ultrasonic detection of blood flow, *IEEE Trans. Biomed. Eng.* BME–34: 965–967; 1987.

Varghese, T.; Ophir, J.; Enhancement of echo–signal correlation in elastography using temporal stretching, *IEEE Trans on Ultras., Ferroel, and Freq. Control* UFFC–44, No.1: 175–180; 1997a.

Varghese, T.; Ophir, J.; A theoretical framework for performance characterization of elastography, *IEEE Trans. Ultrason. Ferroel. Freq. Cont.* 44: 164–172; 1997b.

Wagner, R.F.; Smith, S.W.; Sandrik, J.M. Lopez, H.; Statistics of Speckle in Ultrasound B–Scans, *IEEE Trans. on Son. and Ultras.* 30, No.3: 156–163; 1983.

Wagner, R.F.; Insana M.F.; Smith, S.W.; Fundamental correlation lengths of coherent speckle in medical ultrasonic images, *IEEE Trans on Ultras., Ferroel, and Freq. Control* UFFC–35(1); 1988.

Ophir, J., et al.; Elastography: Ultrasonic Estimation and Imaging of the Elastic Properties of Tissues; *Proc. Instn, Mech. Engrs.*; 213:H, 1999, 203–233.

* cited by examiner

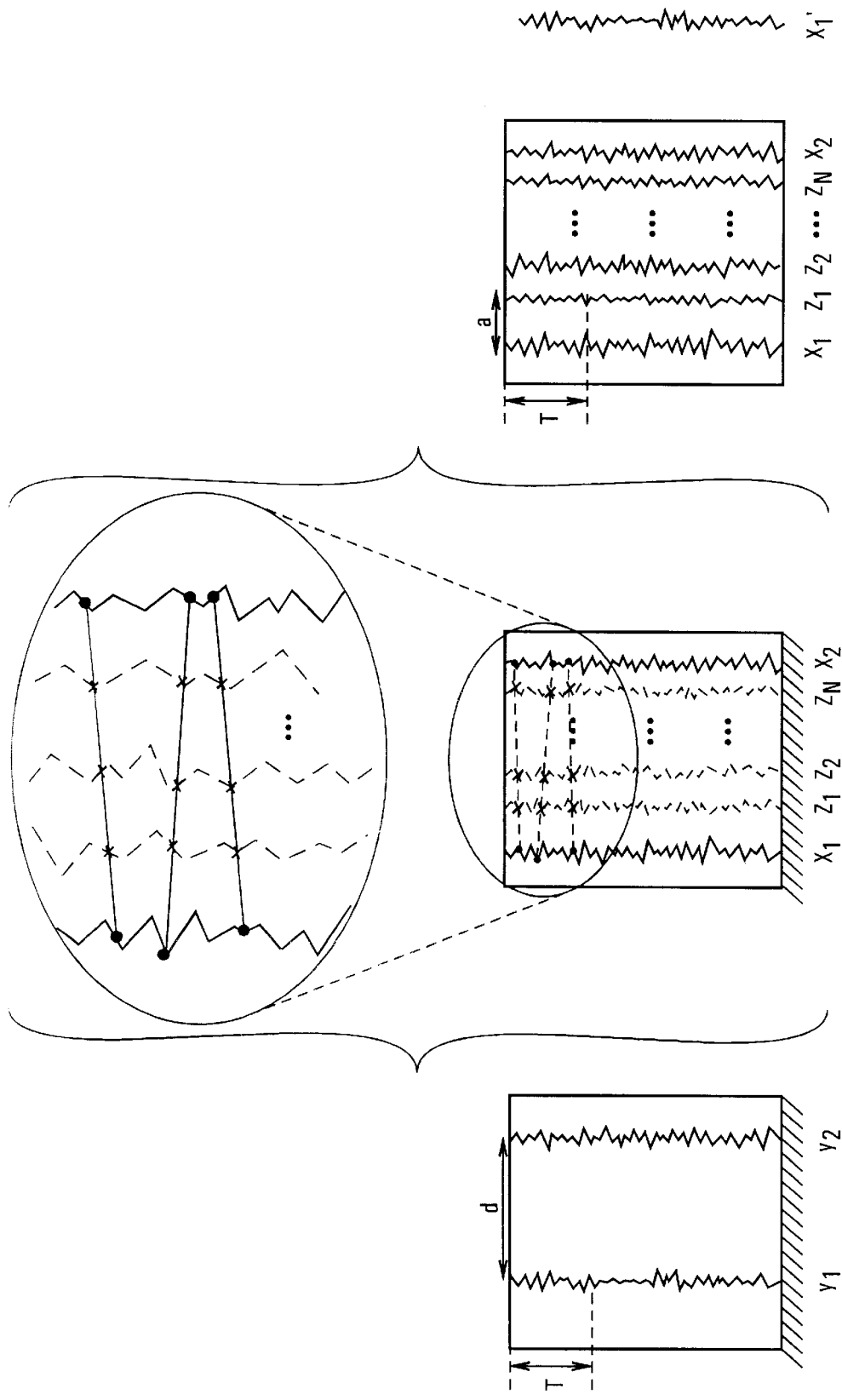

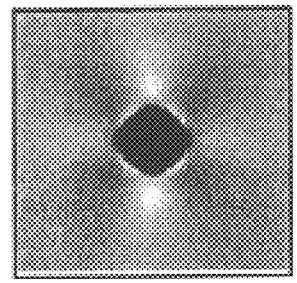
FIG. 8a
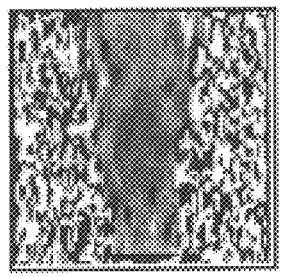 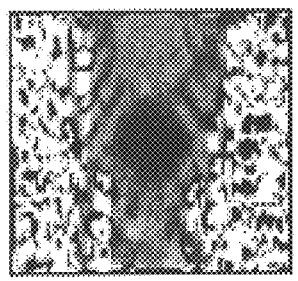 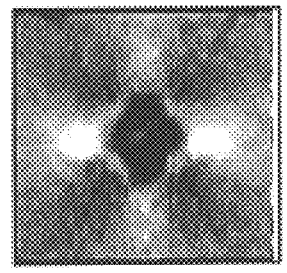
FIG. 8b   FIG. 8c   FIG. 8d

METHOD FOR ESTIMATING AND IMAGING OF TRANSVERSE DISPLACEMENTS, TRANSVERSE STRAINS AND STRAIN RATIOS

CROSS REFERENCE TO RELATED APPLICATIONS

This application is a continuation-in-part of provisional application Ser. No. 60/086,767 which was filed May 26, 1998.

BACKGROUND OF THE INVENTION

1. Field of the Invention

The present invention is directed toward a new method that combines interpolation between neighboring A-lines with cross-correlation for high precision estimation of the transverse displacement. Due to this high precision transverse estimation, the method of the present invention can produce quality transverse-elastograms that display the transverse component of the strain tensor. These higher precision transverse displacement estimates also allow a finer correction for the transverse decorrelation that corrupts the axial estimation. The method of the present invention may be employed to divide the transverse-elastogram by the axial-elastogram on a pixel-by-pixel basis, in order to produce a new image that displays the distribution of strain ratios in the tissue.

2. Description of the Prior Art

Prior art references referred to herein include:

(1) Alam, S. K.; Ophir, J.; Konofagou, E. An adaptive strain estimator for Elastography, IEEE Trans. Ultrason., Ferroel., Freq. Cont.; 1998;

(2) Bamber J. C.; Bush, N. L. Freehand elasticity imaging using speckle decorrelation rate. Acoustical imaging 22: 285–292; 1996;

(3) Bendat J. S.; Piersol, A. G. Random Data, Analysis and Measurement Procedures, John Wiley & Sons, New York, 2nd edition; 1986;

(4) Bohs L. N.; Trahey, G. E. A novel method for angle independent ultrasonic imaging of blood flow and tissue motion. IEEE Trans. Biomed. Eng. 38: 280–286; 1991;

(5) Bohs L. N.; Friemel B. H.; Trahey, G. E. Experimental velocity profiles and volumetric flow via two-dimensional speckle tracking 21(7): 885–898; 1995;

(6) Bonnefous, O. Measurement of the complete (3D) velocity vector of blood flows. Proc. IEEE Ultrason. Symp: 795–799; 1988;

(7) Bonnefous, O. Statistical Analysis and time processes applied to velocity measurement. Proc. IEEE Ultrason. Symp: 887–892; 1989;

(8) Burckhardt, C. B. Speckle in Ultrasound B-Mode Scans. IEEE Trans. on Son. and Ultras. SU-25 (1): 1–6; 1978;

(9) Cespedes, I. and Ophir, J. Reduction of image noise in elastography. Ultrasonic Imaging 5 (2): 89–102; 1993;

(10) Chaturvedi P. Insana M. Hall T. 2D companding for noise reduction in strain imaging. IEEE Trans of Ultras., Ferroel. and Freq. Control; 1998;

(11) Chaturvedi P. Insana M. Hall T. Bilgen, M. 3D companding using linear arrays for improved strain imaging. IEEE Ultras. Symposium; 1997;

(12) Cohn, N. A. Emelianov, S. Y. Lubinski, A. M. O'Donnell M. An Elasticity Microscope, Part I: Methods, IEEE Trans of Ultras., Ferroel. and Freq. Control 44(6): 1304–1319; 1997;

(13) Dotti, D.; Lombardi, R.; Piazzi, P. Vectorial measurement of blood velocity by means of ultrasound. Med. Biol. Eng. Comp 30: 219–225; 1992;

(14) Fung, Y. C. Connecting incremental shear modulus and Poisson's ratio of lung tissue with morphology and rheology of microstructure. Biorheology 26: 279–289; 1989;

(15) Geiman, B. J.; Bohs, L. N.; Anderson M. E.; Czensak, S. P.; Trahey, G. E. 2D vector flow imaging using ensemble tracking: initial results. Ultras. Imag. 18: 61–62; 1996;

(16) Hein, I. A. Multi-directional ultrasonic blood flow measurement with a triple beam lens. Proc. IEEE Ultrason. Symp.: 1065–1069; 1993;

(17) Hein, I. A.; O'Brien, W. D. Current Time-domain Methods for assessing tissue motion by analysis from reflected ultrasound echoes- a review. IEEE Trans on Ultras., Ferroel, and Freq. Control UFFC-40, No.2, 1993;

(18) Insana M.; Chaturvedi P.; Hall T.; Bilgen, M. 3D companding using 1.5D arrays for improved strain imaging. IEEE Ultrason. Symp.; 1997;

(19) Irons, B; Ahmad, A. Techniques of finite elements, Ellis Horwood, p. 461; 1980;

(20) Jensen, J. A. Estimation of blood velocities using ultrasound, Cambridge University Press; 1996;

(21) Jurvelin, J. S.; Buschmann, M. D.; Hunziker, E. B. Optical and mechanical determination of Poisson's ratio of adult bovine humeral articular cartilage. J. Biomechanics 30, No.3: 235–241; 1997;

(22) Kallel F. Proprietes elastiques des tissus mous a partir de l'analyse des changements spatio-temporels dans les signaux ultrasonores. PhD dissertation, Ecole Polytechnique, University of Montreal, Montreal, Quebec, Canada; 1995;

(23) Kallel, F.; Bertrand, M. Tissue elasticity reconstruction using linear perturbation method. IEEE Trans. Med. Imag 15: 299–313; 1996;

(24) Kallel, F.; Ophir, J. Three-dimensional tissue motion and its effect on image noise in elastography. IEEE Trans of Ultras., Ferroel. and Freq. Control 44:1286–1296; 1997a;

(25) Kallel, F.; Varghese, T.; Ophir, J.; Bilgen, M. The nonstationary strain filter in elastography, Part II: Lateral and elevational decorrelation. Ultrasound in Med. and Biol. 23 (9): 1357–1369; 1997;

(26) Kaliel, F.; Ophir, J. Elastographic imaging of low contrast elastic modulus distributions in tissue. IEEE Trans of Ultras., Ferroel. and Freq. Control; 1997b;

(27) Kallel, F.; Bertrand, M.; Ophir, J. Fundamental limitations on the contrast-transfer efficiency in elastography: An analytic study. Ultras. in Med. and Biol 22(4): 463–470; 1996;

(28) Kaliel, F.; Ophir, J. A least squares estimator for elastography. Ultrasonic Imaging; 1997d;

(29) Kino, G. S.; Acoustic waves: devices, imaging and analog signal processing. Prentice Hall; 1987;

(30) Lai W. M.; Rubin D.; Krempl, E. Introduction to Continuum Mechanics. Pergamon Press; 1978;

(31) Lubinski, A. M.; Emelianov, S. Y.; Raghavan, K. R.; Yagle, A. E.; Skovoroda, A. R.; O'Donnell, M. Lateral displacement estimation using tissue incompressibility. IEEE Trans of Ultras., Ferroel. and Freq. Control 43(2); 1996;

(32) Mridha, M.; Odman S. Noninvasive method for assessment of subcutaneous edema. Med. and Biol. Engineering and Computing 24: 393–398; 1986;

(33) Ophir, J.; Johnson, W.; Yazdi, Y.; Shattuck, D.; Mehta, D. Correlation artifacts in speed of sound estimation in scattering media. Ultras. in Med. and Biol. 15 (4): 341–353; 1989;

(34) Ophir, J.; Cespedes, I.; Ponnekanti, H.; Yazdi, Y.; Li, X. Elastography: a quantitative method for imaging the elasticity of biological tissues. Ultrasonic Imaging 13: 111–134; 1991;
(35) Ophir, J; Cespedes, I; Garra, B.; Ponnekanti, H; Huang, Y; Maklad, N; Elastography: ultrasonic imaging of tissue strain and elastic modulus in vivo, European Journal of Ultrasound 3: 49–70;1996;
(36) Ophir, J.; Kallel, F.; Varghese, T.; Bertrand, M.; Cespedes, I.; Ponnekanti, H. Elastography: A systems approach; The Int. J. Imag. Sys. Tech., John Wiley & Sons, Inc 8: 89–103; 1997;
(37) Ramamurthy, B. S.; Trahey, G. E. Potential and limitations of angle-independent flow detection algorithms using radio-frequency and detected echo signals. Ultrasonic imaging 13: 252–268; 1991;
(38) Rice, J. R.; Cleary, M. P. Some basic stress diffusion solutions for fluid-saturated elastic porous media with compressible constituents. Reviews of geophysics and space physics 14(2): 227–241; 1976;
(39) Saada, A. S. Elasticity, theory and applications. New York:Pergamon Press: 377–399; 1989;
(40) Sarvazyan, A. P. Low frequency acoustic properties of biological tissues. Mechanics of polymers 4:691–695; 1975;
(41) Skovoroda, A R; Emelianov, S Y; Lubinski, A M; Sarvazyan, A. P.; O'Donnell, M. Theoretical analysis and verification of ultrasound displacement and strain imaging. IEEE Trans of Ultras., Ferroel. and Freq. Control 41(3); 1994;
(42) Skovoroda, A. R.; Emelianov, S. Y.; O'Donnell, M. Tissue elasticity reconstruction based on ultrasonic displacement and strain images. IEEE Trans of Ultras., Ferroel. and Freq. Control 42: 747–765; 1995;
(43) Sumi C.; Suzuki A.; Nakayama K. Estimation of shear modulus distribution in soft tissue from strain distribution. IEEE Trans Biomed Eng 42:193–202; 1995;
(44) Trahey, G. E. Allison, J. W. von Ramm, O. T. Angle independent ultrasonic detection of blood flow. IEEE Trans. Biomed. Eng. BME-34: 965–967; 1987;
(45) Varghese, T.; Ophir, J. Enhancement of echo-signal correlation in elastography using temporal stretching. IEEE Trans on Ultras., Ferroel, and Freq. Control UFFC-44, No.1: 175–180; 1997a;
(46) Varghese, T.; Ophir, J. A theoretical framework for performance characterization of elastography. IEEE Trans. Ultrason. Ferroel. Freq. Cont. 44: 164–172; 1997b;
(47) Wagner, R. F.; Smith, S. W.; Sandrik, J. M. Lopez, H. Statistics of Speckle in Ultrasound B-Scans. IEEE Trans. on Son. and Ultras. 30, No.3: 156–163; 1983;
(48) Wagner, R. F.; Insana M. F.; Smith, S. W. Fundamental correlation lengths of coherent speckle in medical ultrasonic images. IEEE Trans on Ultras., Ferroel, and Freq. Control UFFC-35(1); 1988; and
(49) U.S. Pat. No. 5,000,184 to Bonnefous.

A major disadvantage of the current practice of elastography is that only the axial component of the strain is used to produce the axial-elastogram. The lateral and elevational components are basically disregarded, yet they corrupt the axial strain estimation by inducing decorrelation noise. In fact, several papers (Lubinski et al. 1996; Cohn et al. 1997; Kallel 1995) in the field disclose or suggest that precision lateral displacement estimation cannot be achieved in the lateral direction. They had neglected the fact that the RF, instead of the envelope of the signal could be tracked.

In elastography, the axial component of the strain tensor is computed by taking the gradient of the axial (along the beam propagation axis) displacement occurring after a quasi-static tissue compression (Ophir et al. 1991; Ophir et al. 1996; Ophir et al. 1997). The estimation of the axial displacement is achieved by using time-delay estimation techniques applied to pre- and postcompression RF A-lines (Ophir et al. 1997). In general, however, the tissue motion that occurs during compression is three-dimensional.

Since the lateral (perpendicular to the beam propagation axis and in the scan plane) and elevational (perpendicular to the beam propagation axis and to the scan plane) motions are not measured, two major drawbacks are encountered. First, the axial-elastogram takes into account only a small part of the mechanical tissue motion information. Second, the unaccounted-for lateral and elevational motions are the primary causes of signal decorrelation (Kallel and Ophir 1997a; Kallel et al. 1997). The lateral or elevational decorrelation can be prevented by appropriate confinement of the tissue under study (Kallel and Ophir 1997a). Confinement may not, however, always be practical in clinical applications, especially when the tissues under study are not easily accessible.

Many publications have dealt with the problem of motion estimation in two-dimensions. Currently, most motion estimators are used to estimate the projection of the motion vector onto the ultrasound beam direction, or to measure only the axial component of the total motion. Initially, multi-dimensional motion estimation started in the field of blood velocity estimation, in order to estimate velocity components, other than the axial one. Later, in the field of elasticity imaging, some of the methods developed in the flow measurement field were borrowed while others developed new techniques, better suitable for elasticity measurements. As detailed below, these fields are different in many ways so that motion estimation algorithms should be shared with caution.

A) Blood flow-velocity estimation

Most of the problems in this field arise from the fact that the scatterers (mainly, the blood cells) to be tracked are fast-moving and their local density as well as orientation are constantly changing during blood flow (Hein and O'Brien 1993). The pulse repetition frequency and the computation speed of the algorithm used for the velocity estimation are, therefore, the most crucial factors, since a high acquisition and/or computation time can significantly limit the maximum velocity that can be measured (Hein and O'Brien 1993; Trahey et al. 1988). Also, given that the blood scatterers have a low echogenicity, the reflected echoes suffer from very low signal-to-noise ratio (SNR). Other limitations include the fact that the adjacent beams have to be as close to parallel as possible in order to estimate the same velocity component as the scatterers move across the beams (Jensen 1996). There have been various techniques proposed for two-dimensional velocity estimation and a few representative ones are mentioned below.

1) Multiple beam approach

Bonnefous (1988) discloses a 3D theoretical blood flow model that included various correlation algorithms and the use of linear interpolation between adjacent signals to detect all three motion components. Lateral beams from different pulse excitations are crosscorrelated to find the lateral displacement of the scatterers between emissions. The model was tested using only simulated data while no experimental results have been reported. Dotti et al. (1992) used a single-element transducer and extended the 1D correlation method into two dimensions using a two-element transducer. Again, by correlating signals between adjacent elements they were able to estimate the lateral flow velocity component. However, the range of lateral velocities that could be accurately measured was limited by having only two lateral measurement positions. Hein (1993) developed a system with a triple-beam ultrasound lens forming three parallel beams, that was able to measure high velocities at large depths. The lateral component was calculated when the blood scatterers would move from beam to beam. The difficulty in the implementation of this method lies in making these beams equal and parallel (Jensen 1996).

2) Speckle tracking method

An alternative to using multiple beams is the speckle tracking method. Trahey et al. (1987) have suggested using the normalized cross-covariance between small rectangles (or kernels) of two successive B-mode frames. The location of the peak in the covariance estimate indicates the amount of displacement of the speckle pattern between frames and is converted to velocity from the knowledge of the time lapse between the two frames. A major disadvantage of this technique is the large amount of calculation required in real-time, making this an impractical algorithm for blood flow measurements.

Therefore, Bohs and Trahey (1991) suggested a faster algorithm that calculates the absolute sum of the pixel differences, or the Sum-of-Absolute-Differences (SAD) algorithm. A comparison of the accuracy of tracking between correlation and SAD showed that both techniques are equally able to track scatterers with comparable accuracy, for both lateral and axial displacements. Also, as expected, it has been shown that RF processing performs more precise tracking than envelope-detected processing (Ramamurthy and Trahey 1991; Bohs and Trahey 1991). More recently, Geiman et al. (1996) have developed a method of ensemble tracking that involves parallel receive processing, 2D pattern matching, and interpolation of the resulting tracking grid to estimated sub-pixel speckle translations between successive ultrasonic acquisitions.

B) Elasticity estimation

Elastography uses a quasi-static compression to induce the strain in the ultrasonically scanned tissue (Ophir et al. 1991). The limitations of the motion estimation in this field are quite different from the ones in the blood flow estimation. Fast acquisition and/or computation may not be as important because the scatterer motion is small and can be controlled by the applied compression. Furthermore, the sonographic signal-to-noise ratio is higher in tissue than in blood by orders of magnitude. Both these factors allow us to aim for high precision of motion estimation and, thus, high elastographic signal-to-noise ratio. While high precision tracking of axial motion has been reported (Ophir et al. 1991; Skovoroda et al. 1994), precision lateral tracking has not been reported.

The speckle tracking method developed by Bohs and Trahey (1991) was used to study the mechanical vibration propagating through tissue (Walker et al. 1992). A similar method, called 2D companding, was recently developed for elastography in order to reduce decorrelation noise in elastograms using applied axial strains of up to 5% and correcting for the lateral decorrelation, if out-of-plane displacement was negligible (Chaturvedi et al. 1998). This method uses speckle block matching techniques (Bohs and Trahey 1991) to track the 2D motion of the scatterers after static compression. It has recently been extended to 3D companding (Chaturvedi et al. 1997) in order to compensate for the elevational displacement as well. The main limitation of this method is that it cannot be used to produce quality lateral elastograms (Chaturvedi et al. 1998), since it is limited by the coarse lateral spacing between elements (defined as pitch) of the ultrasonic array to estimate the lateral displacement. For precision lateral displacement estimation, much finer tracking must be performed. Chaturvedi et al. (1998) attempted to perform interpolation using the Grid Slopes technique described by Geiman et al. (1996) but the gradient calculation involved in the slope estimation introduced large errors.

Lubinski et al. (1996) have shown that when complex baseband data are used to track lateral motion, the variance of the lateral displacement estimation is larger than the variance of the axial displacement estimate by orders of magnitude. They show that lateral displacement images are noisy after using the traditional 2D correlation tracking. Based on these results, they proposed the estimation of lateral displacement by making the assumption of incompressibility of the tissue, and thus making use of the precision of the axial measurement. It is, however, rare that these assumptions are valid at all spatial scales for biological tissues (Chaturvedi, et al. 1998).

SUMMARY OF THE INVENTION

The limits of the aforementioned methods used for lateral displacement estimation are due to simplifying assumptions, such as tissue incompressibility, and the use of an ensemble (kernel) of A-lines (Bohs and Trahey 1991), which limit the precision of lateral tracking. In fact, the speckle tracking technique might be the only solution for velocity measurements. However, in a case such as elasticity imaging, where time and SNR may not be important factors, cross-correlation of single A-lines in the lateral direction and added interpolation techniques to measure subpitch motion can be made. The disclosure of U.S. Pat. No. 5,474,070 is incorporated herein by reference. This patent discloses methods of insonification, cross correlation of signals and elastography.

In a broad embodiment, the method of the present invention comprises (a) acoustically coupling at least two spaced ultrasound sources lying in a transverse plane to the surface of a target body, said sources spaced apart a distance d, such that said beams overlap; (b) emitting a first pulse along the axis of each beam and into the target body; (c) recording the arrival time of the first echo sequence having at least one echo segment arriving in response to said first pulse of ultrasound energy within each beam; (d) emitting a next pulse of ultrasound energy along each beam axis, (e) recording the arrival time of a next echo sequence for each beam emitted in step (d); (f) storing the previously recorded data in a retrievable medium; and (g) finding a match of at least one first echo sequence of a beam emitted in step (a) to next said echo sequence of a beam emitted is step (d).

The present invention may further comprise (h) estimating the transverse displacement(s) from the location(s) of one or more transverse match(es) of step (g); and (i) estimating the slope of the transverse displacement recorded in step (h) to estimate the transverse strain.

The term "transverse plane", as used herein, refers to any plane that is perpendicular to the A-lines of the ultrasound sources. The term "transverse displacement", as used herein, is the displacement between any two points lying in any transverse plane.

DESCRIPTION OF THE DRAWINGS

FIGS. 3a–3d are graphs of A-lines using the method of the present invention.

FIGS. 8a–8d are elastograms using the method of the present invention.

DESCRIPTION OF THE PREFERRED EMBODIMENTS

Figure 1A:
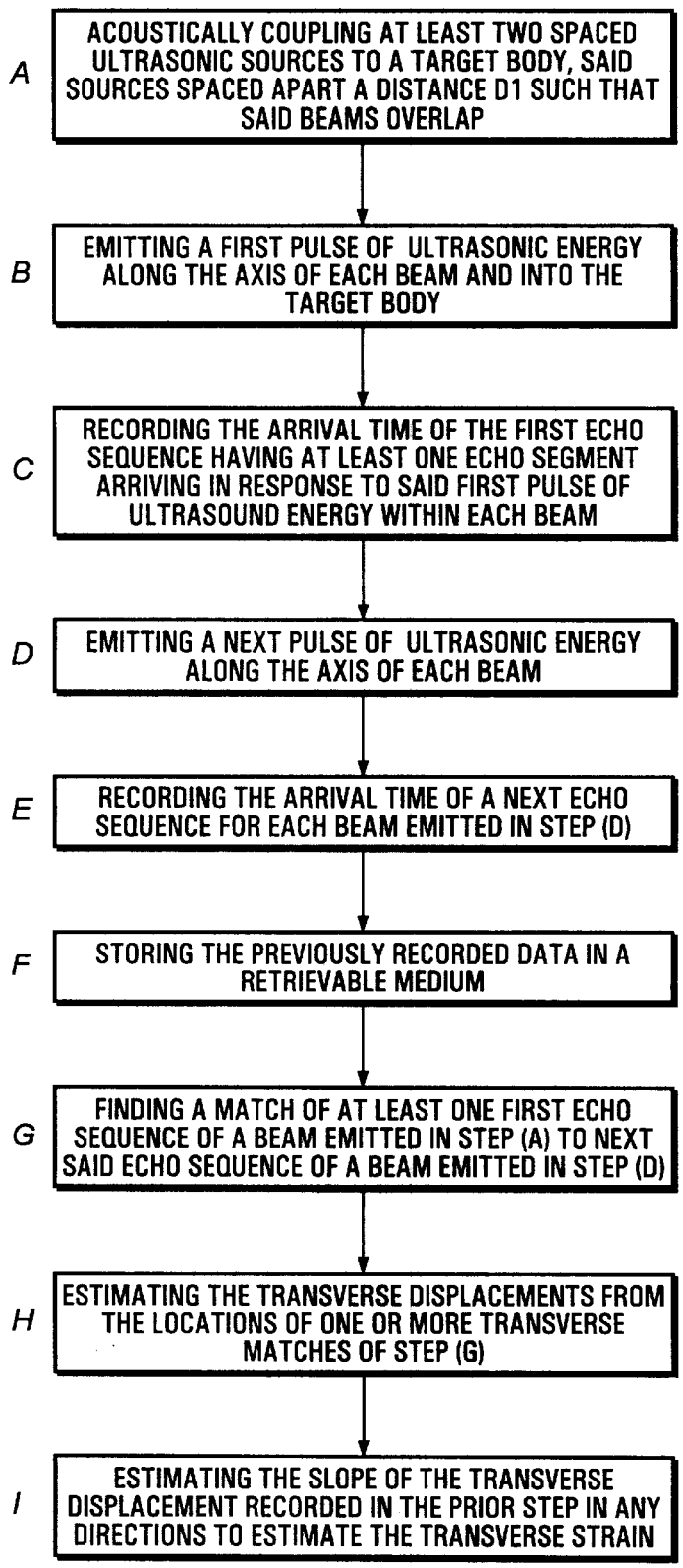
FIG. 1A is a block diagram of a first embodiment of the present invention.

In a first embodiment, the method of the present invention comprises (a) acoustically coupling at least two spaced ultrasound sources to the surface of a target body, said sources spaced apart a distance d, such that said beams overlap and lying in a transverse plane; (b) emitting a first pulse of ultrasound energy along the axis of each beam and into the target body; (c) recording the arrival time of the first RF echo sequence having at least one RF echo segment arriving in response to said first pulse of ultrasound energy within each beam; (d) emitting a next pulse of ultrasound energy along each beam axis, (e) recording the arrival time of a next echo sequence for each beam emitted in step (d); (f) storing the previously recorded data in a retrievable medium; and (g) finding a match of at least one first echo sequence of a beam emitted in step (a) to next said echo sequence of a beam emitted is step (d) as shown in FIG. 1A. In a preferred embodiment, the invention further comprises (h) estimating the transverse displacement(s) from the location(s) of said transverse match(es) of step (g); and (i) estimating the slope of the transverse displacement recorded in step (h) in any direction, to estimate the strain. This method is also depicted in FIG. 1A.

In a preferred embodiment, the invention further comprises (1) estimating the transverse strain, (2) storing data selected from the group of data indicative of estimated transverse strain estimated shear or estimated transverse displacement, (3) repeating steps (1) and (2) for different regions of the body, and (4) displaying the stored data.

Figure 1B:
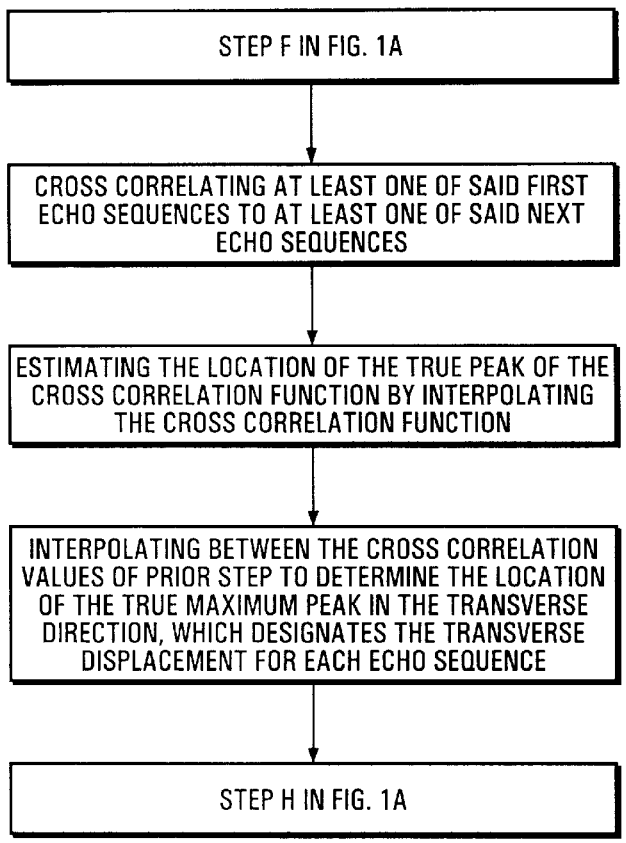
FIG. 1B is a block diagram of a method for conducting the finding step of the present invention.

In a preferred embodiment, the finding step, (g), comprises (a) cross-correlating at least one of said first echo sequences to at least one of said next echo sequences; (b) estimating the location of a peak of the cross-correlation function by interpolating the cross-correlation function; and (c) interpolating between the cross-correlation values obtained of step (b) to determine the location of a peak in the transverse direction, which designates the transverse displacement for each echo sequence as shown in FIG. 1B. The term "cross correlation", as used herein, encompasses autocorrelation, normalized correlation, and unnormalized correlation.

Figure 1C:
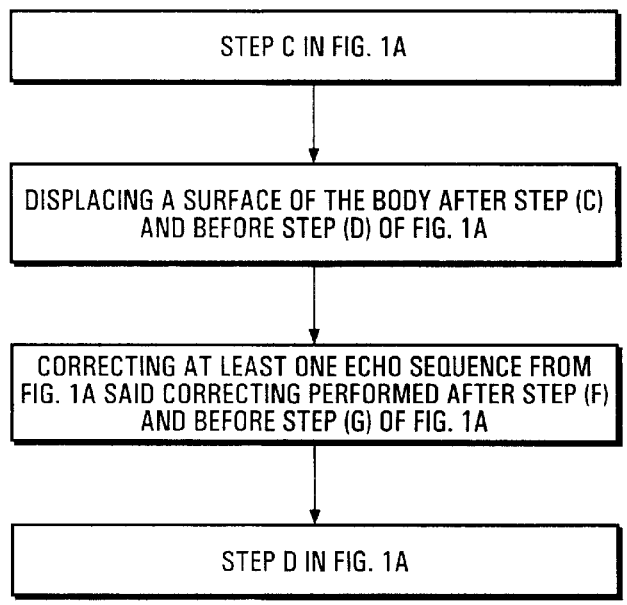
FIG. 1C is a block diagram of the displacing step of the present invention.

In another preferred embodiment, a displacing step is practiced between steps (c) and (d). The displacing step comprises displacing a surface of the target body as shown in FIG. 1C. The surface may be external or internal.

In another preferred embodiment, the method of the present invention may further comprise the step of correcting at least one echo sequence shown in FIG. 1A in FIG. 1C. In this embodiment, the aforementioned step should be practiced between steps (f) and (g), as defined above.

Figure 1D:
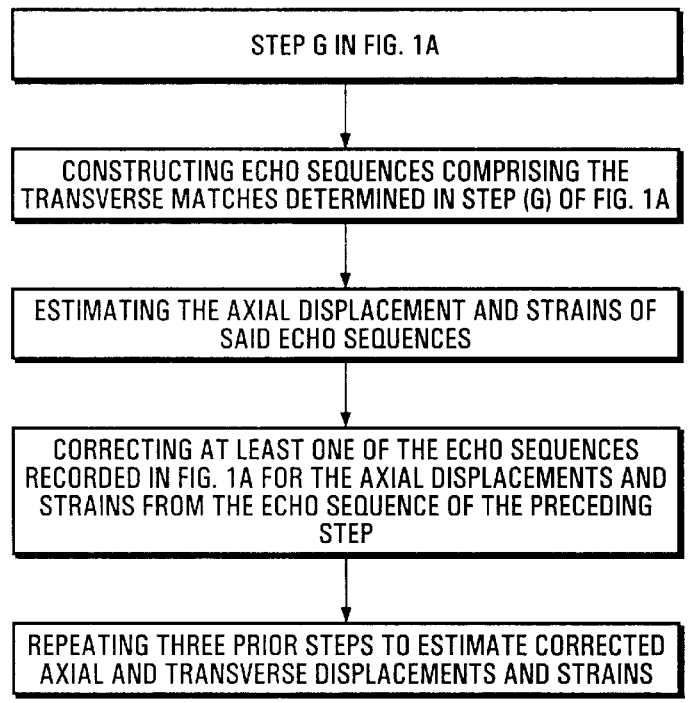
FIG. 1D is a block diagram of the transverse and axial motion correction steps of the present invention.

In addition to steps (a)–(i), set forth above, a preferred embodiment of the present invention may further comprise (j) constructing echo sequences comprising the transverse matches determined in step (g); (k) estimating the axial displacements and strains of the new echo sequences of step 0); (l) correcting at least one of said echo sequences recorded in steps (a)–(g), for the axial displacements and strains from the echo sequence of step (k); (m) repeating steps (j) through (l) to estimate the axial and transverse displacements and strains; and (n) displaying axial and transverse strains, as shown in FIG. 1D.

Figure 1E:
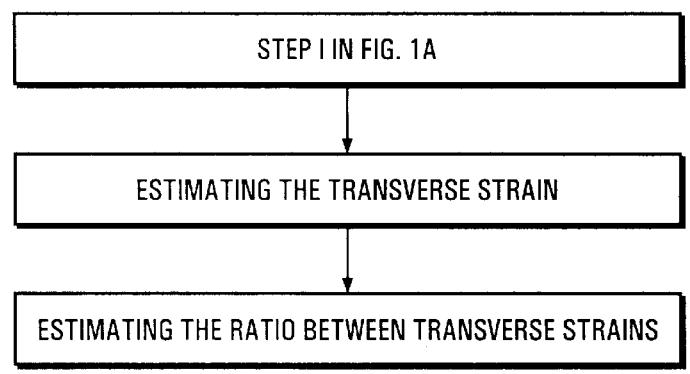
FIG. 1E is a block diagram of the ratio estimating and imaging step of the present invention.

In another preferred embodiment, the method defined by steps (a)–(i) further comprises estimating the transverse strain, and estimating the ratio between the transverse and axial strain as shown in FIG. 1E. In another preferred embodiment, a step of moving the target body transversely to the beam is practiced between steps (c) and (d).

Figure 1F:
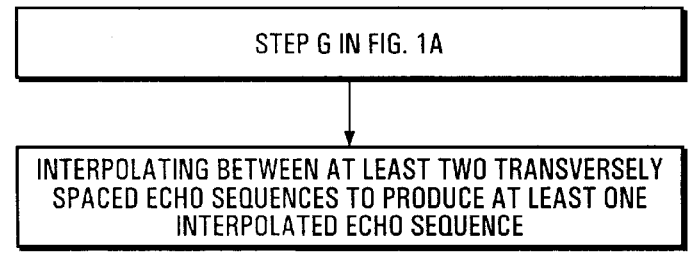
FIG. 1F is a block diagram of the interpolating step of the present invention.

In addition to steps (a)–(i), set forth above, the method of the present invention may further comprise the step of interpolating between two transversely spaced echo sequences to produce at least one interpolated echo sequence as shown in FIG. 1F. In this embodiment, the aforementioned step should be practiced between steps (f) and (g), as defined above.

The present invention comprises tracking the phase of single A-line segments in the lateral direction through the use of interpolation and cross-correlation methods to estimate the lateral component of the strain. Tracking the phase instead of the envelope leads to much higher precision, due to the cyclic nature of the RF (or phase precision), which disappears in the envelope detection process. This phase information contributes to the uniqueness of the speckle patterns that increases the probability of finding a correct match (Hein and O'Brien 1993). In addition, tracking of single A-lines, instead of an ensemble (Bohs and Trahey 1991, Chaturvedi et al. 1998), improves the resolution of the lateral tracking. This method does not make any assumptions about the elastic properties of the tissue under study like the incompressibility method (Lubinski et al. 1996). In fact, the lack of such assumptions allows us to estimate and image an important mechanical parameter of the tissue, the Poisson's ratio, as it is discussed later.

Interpolation techniques can help reconstruct an RF signal in the lateral direction provided that lateral sampling is sufficient. This means that if there is sufficient overlap between the beams in the lateral direction, interpolation methods may be used to overcome the poor ability to track lateral motion that is encountered when using the envelopes of speckle signals as reported by Lubinski et al. 1996 and Kallel 1995.

There are three important advantages in the use of high precision lateral tracking. First, it significantly reduces the variance of the lateral strain estimates, thereby allowing us to obtain new lateral-elastograms, depicting the lateral strain distribution with good precision. Second, it allows for fine correction of the axial-elastogram for high or low strains. This step produces an axial-elastogram with significantly reduced overall decorrelation noise. Thirdly, the lateral-elastogram may be used together with the axial-elastogram to generate an image of the local distribution of an independent major elasticity parameter, the Poisson's ratio (v) which is defined as $$v = -\frac{\varepsilon_l}{\varepsilon_a} \quad (1)$$

where $\varepsilon_l$ and $\varepsilon_a$ are the lateral and axial strains, respectively (Lai et al 1978). The strain ratio is the ratio between any two orthogonal strains. If the strain lies along an axis which is not parallel to the axial dimension, and which does not lie in a transverse plane, vector components of the strain may be determined for use with equation (1) to determine the Poisson's ratio.

As equation (1) shows, the Poisson's ratio is a special case of the strain ratio. The Poisson's ratio describes the coupling between the lateral and axial strains. In plane-strain problems a value of 0.5 means a maximum coupling, while a value of 0 means no coupling. In order to produce quality images of the Poisson's ratio distribution in the tissue, it is preferred that the lateral strain be estimated with precision and resolution that are comparable to those obtainable for the axial strain estimates.

In a preferred embodiment, the present invention also encompasses (a) estimating the strain ratio, (b) storing the estimated strain ratio in the form of strain ratio data, (c) repeating steps (a) and (b) for different regions in the target body; and (d) displaying the stored data.

The Young's modulus (E) and the Poisson's ratio are the two major technical parameters that uniquely describe the elastic properties of isotropic materials. They are derived from the Lame constants (Saada 1989) viz.

$$\mu = \frac{E}{2(1+v)} \text{ and } \lambda = \frac{Ev}{(1+v)(1-2v)} \quad (2)$$

Displaying the Poisson's ratio of the various tissue elements may allow differentiation among dissimilar normal tissues, as well as between normal and abnormal tissues. Rice and Cleary (1976) defined two types of Poisson's ratios in poroelastic materials: the drained and undrained Poisson's ratios, depending on the duration of the compression. If the measurement is done immediately after loading, the Poisson's ratio is high. However, if the measurement is made after a relatively short time, allowing some unbound fluid to leave the material, the Poisson's ratio is reduced according to the amount of fluid leaving the tissue after the compression. Imaging the distribution of Poisson's ratios in tissues may allow the visualization of the water-holding capacity of unbound water in various normal and edematous tissues. Moreover, the changes in the local Poisson's ratios may indicate the quantitative changes in the local fluid volume in the tissue elements.

Since the Poisson's ratio is estimated simply from the ratio of lateral to axial strain in any given pixel (for a plane strain state), it is unaffected by boundary conditions, in as much as both strain components are equally affected.

Due to the large variety of tissue types (both normal and abnormal), the assumption of incompressibility may not hold in various cases (Fung 1989; Jurvelin et al. 1997). There are no definite measurements of the Poisson's ratios found in tissues that are of interest in elastography, such as the breast and the prostate.

Table I, taken from Irons and Ahmad 1980, provides a clearer picture of how the Poisson's ratio varies in different materials. Due to the relatively small dynamic range of Poisson's ratios, the imaging contrast may be limited. However, in elastography it has been shown that low modulus contrast is not an important limitation (Kallel and Ophir 1997b). The use of the lateral motion correction has been shown by Chaturvedi (1998), to improve the contrast-to-noise performance of axial elastograms; thereby improving the ability to visualize low contrast targets.

TABLE I

| Material | Poisson's Ratio |
|---|---|
| Concrete | 0.1–0.15 |
| Steel | 0.3 |
| Aluminum | 0.33 |
| Soft rubber | 0.495 |

Figure 1G:
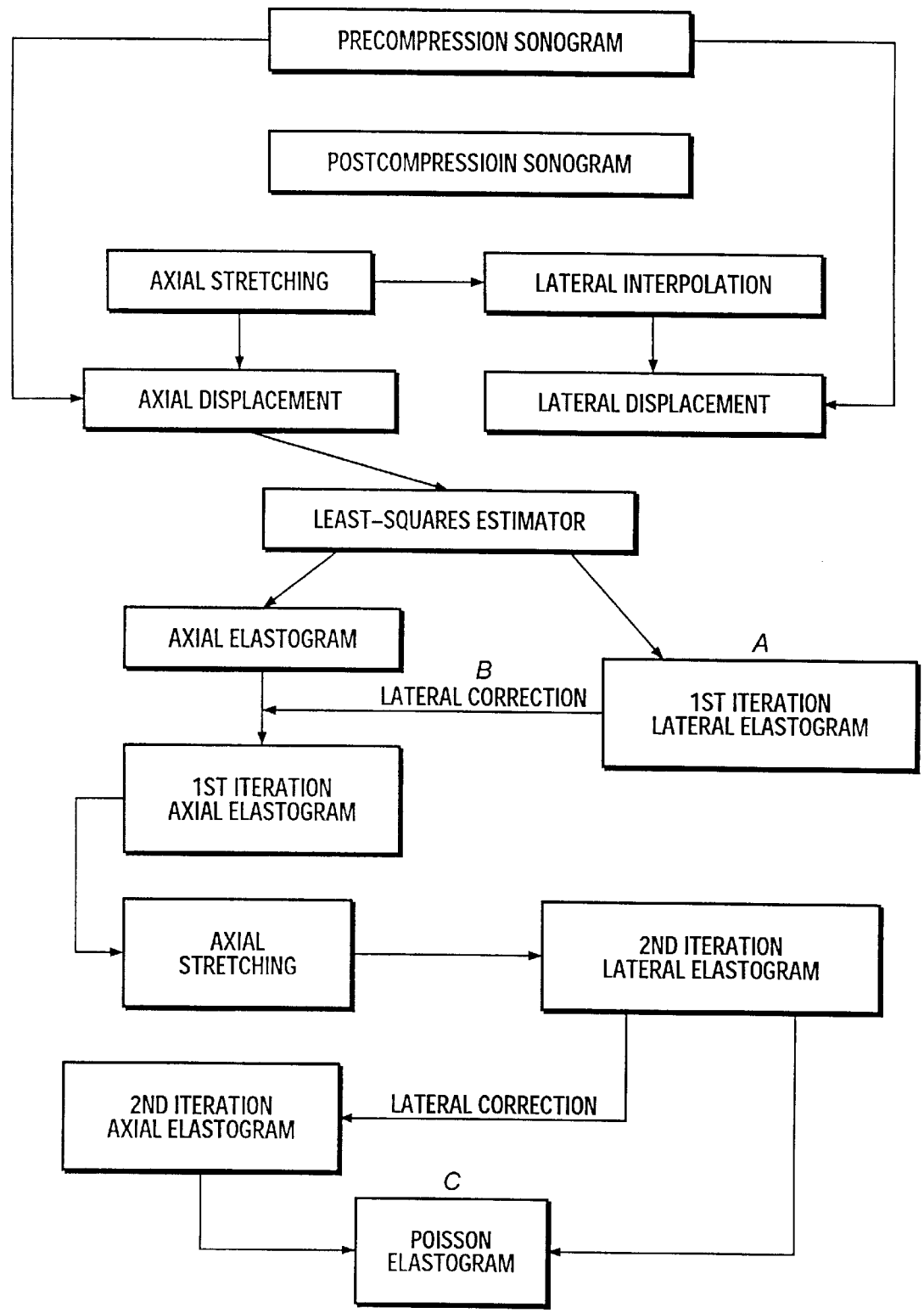
FIG. 1G is a block diagram of a second embodiment of the present invention.

In a preferred embodiment, the method of the present invention comprises the following steps. The postcompression RF A-lines are first globally stretched axially to compensate for the applied strain (Céspedes and Ophir 1993; Varghese and Ophir 1996), and an axial-elastogram is generated; more A-lines are then created by a process of weighted interpolation; and tissue motion is tracked laterally in order to generate a lateral-elastogram (FIG. 1G, step A). The tracked segments are shifted to their assumed precompressed position by the estimated amount of lateral displacement (FIG. 1G, step B) and new corrected postcompression RF A-lines are constructed. This allows for the axial-elastogram to be recomputed. This procedure may be iterated until the correlation coefficient of the axial strain estimation stabilizes at a high value. Finally, the lateral-elastogram is divided by the axial-elastogram to generate a Poisson's-ratio-elastogram (FIG. 1G, step C). All these steps are described in detail in the following section.

Since most clinical systems are using low cost transducers with a small number of channels, i.e., a large pitch (the distance between adjacent beams between transducer elements), the sampling in the lateral direction is often not high enough to allow good lateral tracking or, in the case of elastography, estimation of lateral displacements with high precision. However, if there is sufficient beam overlap, the sampling frequency in the lateral direction may be high enough to reconstruct the "lateral signal" from its samples.

The point-spread function (psf) of the system may be written as a separable function in the focal area, viz.

$$p(x,y) = p_a(x)p_1(y) \quad (3)$$

where $p_a(x)$ and $p_1(x)$ are the axial and lateral psf components, respectively. If we assume a Gaussian modulated emitted pulse, the axial psf component becomes $$P_a(x) = Ae^{\frac{x^2}{2\sigma_x^2}} \cos\left(2\pi \frac{x}{\lambda}\right) \qquad (4)$$

and the lateral psf component of an unapodized, boxcar transducer aperture (not considering grating lobes) is $$P_1(y) = \left(\frac{\sin\left[\frac{\pi D y}{\lambda x_r}\right]}{\left[\frac{\pi D y}{\lambda x_r}\right]}\right)^2 = \left(\frac{\sin\left[\frac{\pi y}{\lambda F}\right]}{\left[\frac{\pi y}{\lambda F}\right]}\right)^2 \qquad (5)$$

where is the axial coordinate, $\sigma_x$ is the pulse length in mm, $\lambda$ is the central wavelength of the emitted pulse, D is the azimuthal aperture width, y is the lateral coordinate, $x_r$ is the focal length and F is the F number of the transducer given by $$F = \frac{x_r}{D} \qquad (6)$$

Figure 2:
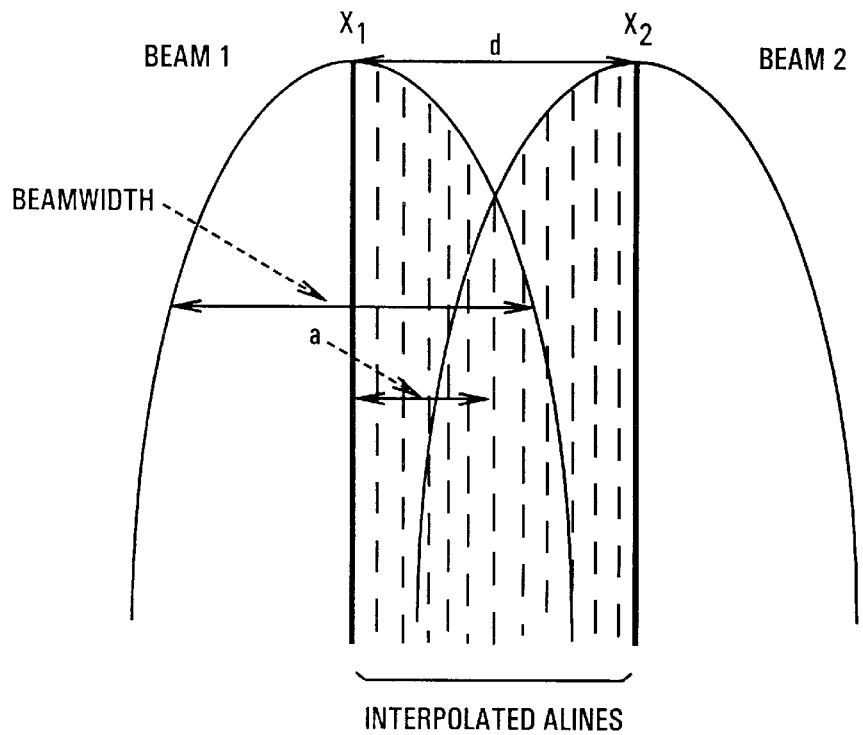
FIG. 2 is a side sectional view of the emitting step of the present invention.

The methods of lateral tracking and lateral correction for two adjacent ultrasound beams, as shown in FIG. 2, are described below.

1) Lateral tracking

Step 1: Linear Interpolation N:1

The postcompression A-lines are first globally stretched axially by the amount of the axial strain applied (Varghese and Ophir 1996). Using a scheme of N:1 linear interpolation generates N A-lines (dotted lines in FIG. 3) between adjacent original postcompression A-lines 1 and 2 (denoted $x_1$ and $x_2$, respectively in FIG. 3) through linear interpolation, described by $$z_{nj} = \frac{a}{d} x_{1j} + \left(1 - \frac{a}{d}\right) x_{2j}, \qquad (7)$$

where $z_{nj}$ is the $j^{th}$ sample on the $n^{th}$ A-line generated, $x_{1j}$ is the $j^{th}$ sample on A-line $x_1$, $x_{2j}$ is the $j^{th}$ sample on A-line $x_2$, a is the distance between $x_{1j}$ and $z_{nj}$ and d is the pitch (FIG. 3). As shown in FIG. 3b, the samples of the original A-lines define the line on which the interpolated samples are generated. The lateral coordinate of the samples generated with interpolation is equal to distance a in Eq. 7 and the axial coordinate is the same as the samples of the original A-lines used to perform the interpolation of Eq. 7.

If the displacement to be measured is higher than the distance separating the two adjacent beams 1 and 2, the interpolation is no longer performed between adjacent beams 1 and 2 but between beam 1 and the beam that is the closest to beam 1, yet at a distance away that is larger than the displacement to be measured.

Step 2: Computation of Cross-correlation Coefficient Function to Approximate the psf We assumed that the psf is not known, as is the case in an experimental study. Therefore, we estimate the psf statistically by computing the maximum of the cross-correlation coefficient-squared between the original A-lines $x_1$ and $x_2$ and all the A-lines generated with linear interpolation. The cross-correlation coefficient-squared $\rho^2_{ni}$ of linearly interpolated A-line n with original A-line i is given by (Bendat and Piersol 1986)

$$\rho^2_{ni} = \frac{C^2_{ni}}{R_{nn} R_{ii}} \qquad (8)$$

where $C_{ni}$ is the cross-correlation of the original A-line i with interpolated A-line n and $R_{ii}$ and $R_{nn}$ are the autocorrelation functions of A-lines i and n, respectively.

Step 3: Weighted Interpolation N:1

The maxima of the correlation coefficients-squared provide the essential information for the characteristics of the linearly interpolated A-lines. The reason for using the correlation coefficient-squared is because it is the explained proportion of the total variation. They are, thus, used as weights for the computation of the final (weight-interpolated) A-lines so that these have their shape weighted according to their location with respect to the original A-lines (determined by the parameter a in Eq.7). For example, if an A-line Zn generated in Step 1 is closer to the original A-line $x_1$ than A-line $x_2$, the correlation coefficient of that A-line with $x_1$ will be higher than $x_1$ and its shape after weighted interpolation will be more correlated to the shape of $x_1$ than of $x_2$. The algorithm performs the weighted interpolation and recomputes A-lines $z_n$ with their $j^{th}$ sample given by $$z_{nj} = \frac{\max(\rho_1^2 n) x_{1j} + \max(\rho_2^2 n) x_{2j}}{\max(\max(\rho_1^2 n), \max(\rho_2^2 n))} \qquad (9)$$

where max(f(x)) denotes the maximum value of the function f(x).

Step 4: Lateral Displacement and Strain Estimation

The purpose of this step is to track the lateral motion of the scatterers after the compression. We thus cross-correlate small segments of each precompression A-line (FIG. 3a) with segments of A-lines generated via weighted interpolation (FIG. 3c), which are found on the same lateral level. The lateral displacement is indicated by the maximum of the cross-correlation coefficient function between the precompression A-line and the post compression interpolated A-lines. The sensitivity (i.e., the smallest lateral displacement that can be measured) is determined by the ratio pitch/N in the case of a N:1 interpolation, providing this method of lateral tracking with high precision as the interpolation scheme increases. This means that this method, unlike other proposed methods, such as 2D companding (Chaturvedi et al. 1998), is not pitch-limited but interpolation noise limited. A preliminary simulation study (in the methods section) provides more insight in the variance of this estimator, but a more thorough study is the subject of current investigations. The lateral strain is estimated from the lateral displacement using a least-squares algorithm (Kallel and Ophir 1997d).

2) Lateral Correction

This step uses the information of lateral displacement of Step 5 of the lateral tracking method to shift the tracked segments by the amount of displacement estimated. FIG. 3d shows an example of lateral correction for this lateral motion.

As expected, the performance of the interpolation method depends on the ultrasonic parameters of the system, such as the pitch, the beamwidth, the overlap, and the mechanical parameters, such as the Young's modulus, the applied axial displacement and the Poisson's ratio. This is because all the aforementioned parameters determine the characteristics of the motion of the scatterers across the beam. The beam width (BW) for a rectangular focused transducer at zero beam level at the focus is equal to (Kino 1987)

$$BW = 2F\lambda. \tag{10}$$

The percent beam overlap is found by $$\% \text{ overlap} = \left(1 - \frac{\text{pitch}}{BW}\right) 100\% \tag{11}$$

What allows us to track laterally using interpolation is the fact that the lateral spatial sampling frequency is above the Nyquist frequency when the percent beam overlap is over 50%. Assuming that the lateral psf component is given by Eq. 5, then its Fourier transform is a triangular function (Wagner et al. 1988). The maximum spatial frequency of this spectrum is $$f_0 = \frac{1}{2F\lambda} \tag{12}$$

According to the Sampling Theorem the sampling spatial frequency, denote $f_{sl}$, should satisfy $$f_{sl} \geq 2f_0. \tag{13}$$

Assuming the pitch is the spatial sampling period (or the inverse of the width of the frequency response at zero frequency) and noting from Eqs. 9 and 11 that the maximum frequency is the inverse of the beamwidth, from Eq.13 we obtain that lateral sampling is sufficient as long as $$\text{pitch} \leq \frac{BW}{2} \tag{14}$$

or, from Eq. 11, when $$\% \text{overlap} \geq 50\% \tag{15}$$

This result means that there is have to be at least 2 A-lines/beamwidth so that lateral interpolation can be performed.

In order to estimate the performance of the algorithm according to both ultrasonic and mechanical parameters, we define a relative measure of the tracking ability, defined as the −6 dB lateral width of the autocorrelation function of the residuals of the linear regression fit to the lateral displacement line (Ophir et al. 1989). These authors have shown that the variance of the residuals is proportional to the square of the autocorrelation width of the residuals. Thus, the wider the autocorrelation function of the residuals, the poorer is the precision of the method in tracking the lateral displacement.

The lateral tracking algorithm allows one to obtain lateral-elastograms, to correct the axial displacement measurements for the laterally induced decorrelation, and to generate Poisson-elastograms. We divide this section accordingly into these three steps.

1) Lateral Elastograms (FIG. 1 G, step A)
a) Homogeneous Case (Finite-Element Simulation)

First, we assessed the dependence of the performance of the algorithm on the following parameters: beamwidth, beam-overlap, the lateral applied strain and the interpolation scheme. The simulated ultrasound beam was generated from Eqs. (2), (3) and (4) assuming, therefore, that the transducer is in the focus at all depths. This is an approximation of the experimental case where transducers have tracking foci. The beamwidth was determined from Eq. 10 for a 5 MHZ transducer and for a particular F-number. The pitch was kept constant at a typical value of 0.4 mm (100 A-lines digitized at 48 MHZ for scanning a tissue with a lateral dimension of 40 mm). These parameters were selected to correspond to our experimental Diasonics Spectra ultrasound scanner, operating at 5 MHZ.

Although no random noise was added to the signals, our studies show that performance of the interpolation method does not degrade significantly for a sonographic SNR larger than 30 dB, which is the usual case for elastographic experiments. A 64:1 interpolation scheme was used. The algorithm was tested on a finite-element simulated homogeneous phantom with a Poisson's ratio of 0.495, generated using the finite element software ALGOR®, available from Algor, Inc. A plane-strain state model was used that disregarded any motion in the elevational direction. Furthermore, a displacement in the lateral direction only was applied. This was done in order to initially separate the effects of the axial from those of the lateral displacements.

In this first part of the study, we perform the lateral tracking of the entire A-line as it moves laterally. This is because we have defined perfect slip conditions and a homogeneous target and, therefore, the whole A-line moves uniformly in the lateral direction. Tracking the entire A-line means the use of the largest tracking window possible, which in turn helps decrease the variance error in the displacement estimation. The homogeneous finite-element simulated tissue phantom had a stiffness of 21 kPa and a Poisson's ratio equal to 0.495. From Table II (detailed later) we concluded that an optimal case would be a 1% lateral applied strain with a beamwidth equal to 1 mm (%overlap= 60%).

In a second part of this study we generated a 2D lateral strain image of the same simulated target. In order to do this, small A-line segments were tracked individually, with an axial window size of 3 mm and overlap of 75%.

b) Homogeneous Case (Experiment)

The ultrasound system consisted of a Diasonics Spectra II scanner (Diasonics Inc., Santa Clara, Calif.), used with a 5 MHZ linear array and a digitizer (LeCroy Corp., Spring Valley, N.Y.) that digitizes (8 bits) the RF A-lines at 48 MHZ. The transducer used has a tracking focus. Kallel and Ophir (1997a) measured the beamwidth of this scanner to equal 2 mm at the focus for 5 MHZ. According to Eq. 11, the percent beam overlap is on the order of 80%, providing more than sufficient lateral sampling to perform interpolation (see Eq.15). A personal computer controls the operation of the motion control system to perform the compression and the data acquisition. A homogeneous gelatin phantom that contains small graphite flakes was used. The phantom was lubricated with oil to achieve slip boundary conditions and confined in the elevational direction in order to simulate plane strain state conditions. It was compressed axially by 1% using a circular compressor of a size smaller than the lateral dimension of the phantom but larger than the transducer. A 64:1 interpolation scheme was used. Global axial stretching was used (Varghese and Ophir 1997a) before using the lateral tracking algorithm.

2) Correction of Axial-Elastograms For Lateral Motion (FIG. 1G, step B)

The same lateral tracking method was applied in the case of an analytic model of the elasticity equation derived for an infinite medium containing a circular inclusion in the center (Kallel et al. 1996). For the computer simulation a region of interest of 40×40 mm was selected and the inclusion diameter was 10 mm. The inclusion was twice as hard as the background with Poisson's ratios of either 0.3 or 0.495. The applied strain was relatively large (3%) so as to demonstrate the importance of the correction.

In order to form the lateral-elastogram an axial window of size equal to 3 mm with 0.75% (axial) overlap was used in all cases to perform lateral tracking (with 64:1 interpolation). The goals were to obtain a high precision lateral elastogram and to correct the axial-elastogram for lateral decorrelation. The lateral correction was performed as shown in FIG. 3. The segments tracked laterally were shifted by the measured amount of lateral displacement in order to synthesize postcompression A-lines as close to the precompression A-lines as possible. This was expected to improve the axial correlation coefficient significantly and therefore the signal-tonoise ratio of the corrected axial elastogram.

3) Poisson-Elastograms (FIG. 1G, step C)

Ultimately, the aim was to investigate the ability of the Poisson-elastogram to show new "tissue" information that could not be seen on either axial or lateral-elastograms. For this purpose, we considered two separate cases of the analytic model of an inclusion embedded in a homogeneous background: one without and one with a Poisson's ratio contrast between the inclusion and the background. In the first case the inclusion and the background have equal Poisson's ratios of 0.495. In biomechanical terms, both inclusion and the background were considered incompressible. In the second case, the inclusion was no longer incompressible, having a Poisson's ratio of 0.3, while the background remained incompressible. In both cases the Young's modulus contrast was set to be equal to two, with the inclusion being twice as hard as the background (the background Young's modulus was 21 kPa). The mechanical as well as ultrasound parameters were identical to the previously described case.

The Poisson-elastograms were generated by dividing the lateral-elastograms by the corrected axial-elastograms, as indicated by Eq.1. The axial-elastograms used were corrected for lateral decorrelation (as described in the previous section) and generated using the same axial window of 3 mm and with a window overlap of 75%. Least-squares smoothing (Kallel and Ophir 1997d) with a kernel size of 10 points was used to smooth both the axial and lateral elastograms. Since the pitch is equal to 0.4 mm, using a 10-point least-squares approximation is equivalent to a 4 mm lateral window. This lateral window size is on the same order as the one typically used for the generation of axial-elastograms.

The Poisson's ratio may also be estimated for a poroelastic/viscoelastic material. The Poisson's ratio of a poroelastic material (FIG. 13) can be measured following the procedure below. The same procedure applies in the case of viscoelastic material.

1. Acquire first sonogram prior to compression;
2. Acquire second sonogram after a given amount of compression;
3. While sustaining the compression at the same applied amount, keep acquiring sonographic data at regular time intervals;
4. Estimate the strain ratio as described before for the Poisson's ratio by using the precompressed sonogram and all the subsequent postcompressed sonograms; and
5. Plot the strain ratio near the flow region with time and estimate time constant.

Sonograms may be acquired by recording the arrival time of an echo sequence resulting from an emitted pulse of ultrasound energy.

Figure 13:
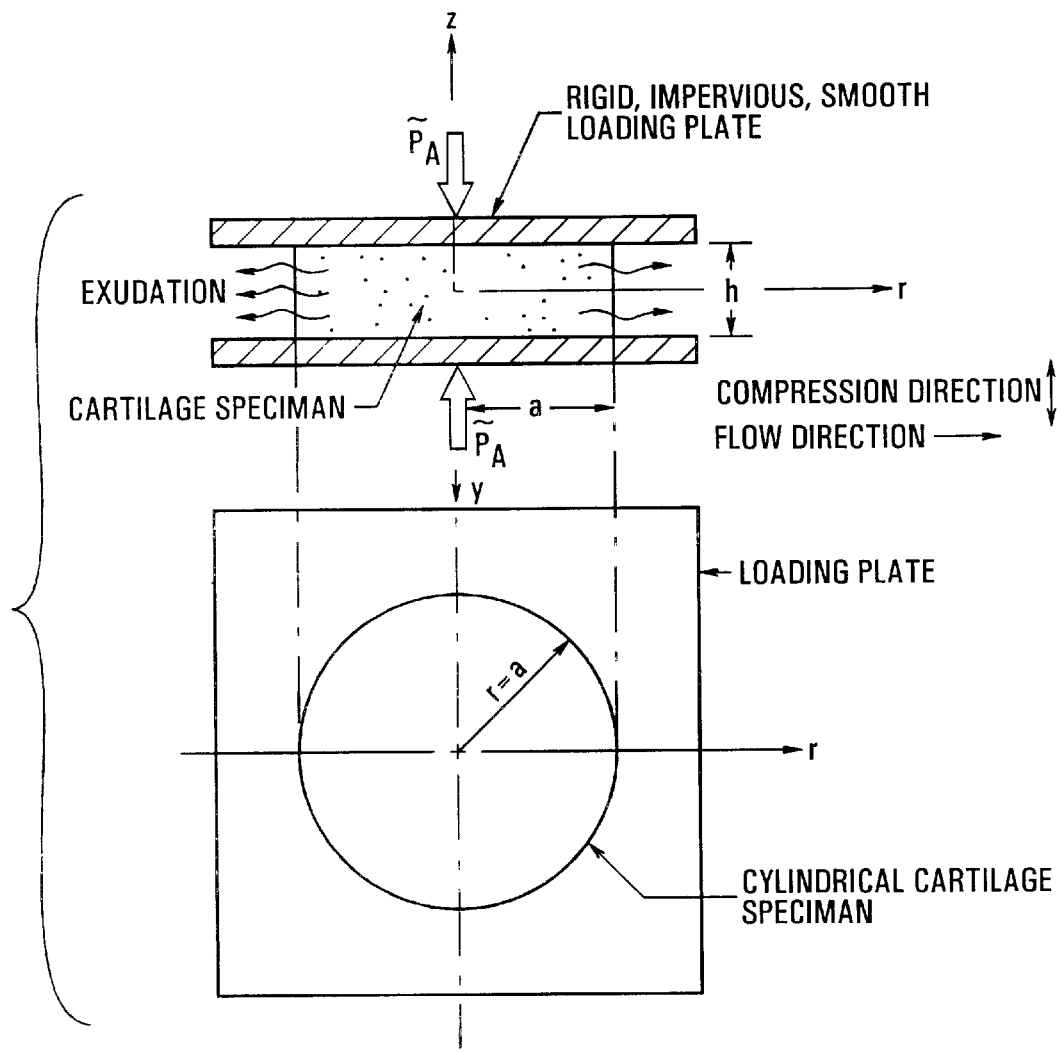
FIG. 13 is a schematic representation of a specimen of biphasic material compressed by two rigid impervious smooth plates.

Results have been obtained with simulations and presented herewith. A 2D finite-element axisymmetric model of a homogeneous linear elastic solid with a Young's modulus equal to 689.5 GPa and a Poisson's ratio vs containing a pore fluid with a permeability equal to 8.47 nm/sec was used. The finite-element model was built on ABAQUS software Version 5.5 based on an example of the Terzaghi consolidation problem (Terzaghi and Peck, 1948) modified for a stress relaxation case. ABAQUS software is available from Hibbift, Karlsson & Sorenson, Inc. of Pawtucket, RI. In this example, the applied strain causes pore pressure to rise initially; then, as the solid skeleton continues to be strained, the pore pressures decay as the solid consolidates, or as the fluid is fully removed. Fluid is allowed to permeate only from the lateral sides of the material while being compressed axially by impermeable plates (FIG. 13). Therefore, the axial strain remains identical with time while the lateral strain drops with time according to the Poisson's ratio of the solid.

Figure 14:
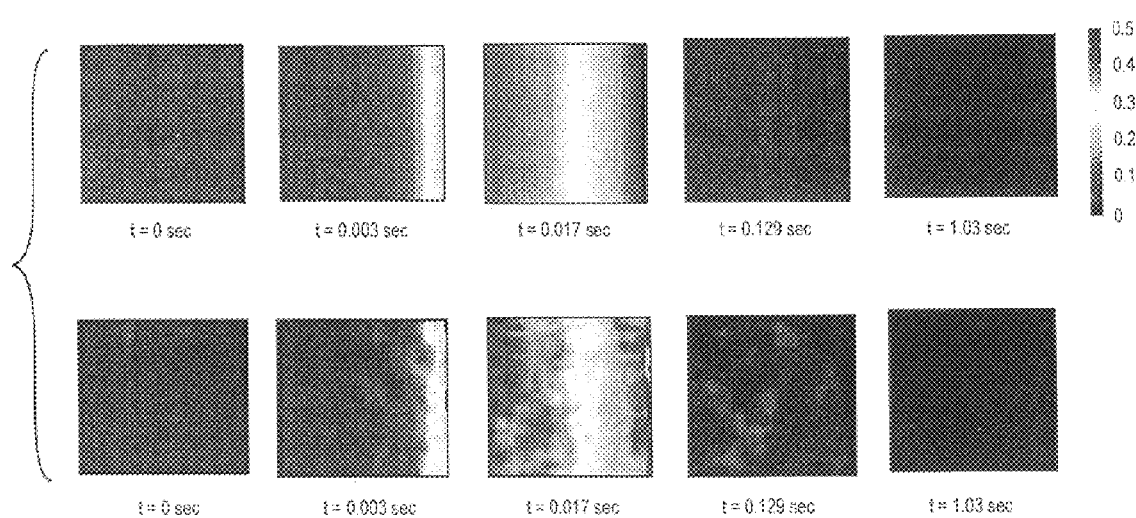
FIG. 14 depicts true and estimated strain ratios as a function of time.

FIG. 14 shows an example of the strain ratio variation over a given time period for a Poisson's ratio of the solid matrix equal to 0.0. An applied strain of 5% was sustained over a certain time course and the lateral displacement at the boundary (normalized by the applied axial strain) is shown over this time as it reduces approaching the value of the Poisson's ratio of the solid matrix.

Figure 15:
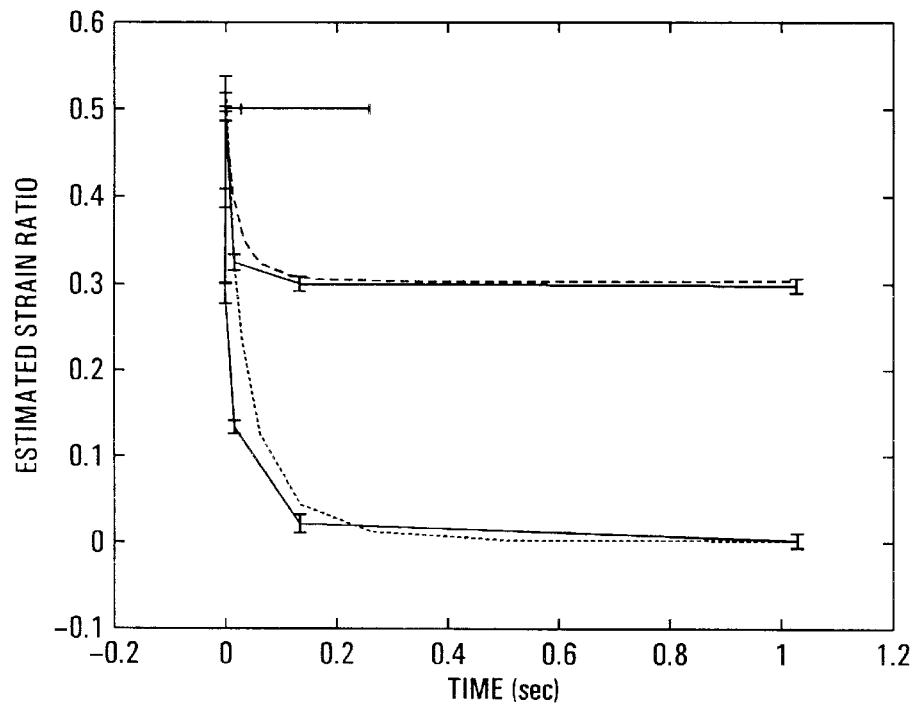
FIG. 15 is a graph of estimated strain ratio as a function of time for various Poisson's ratios.

FIG. 15 summarizes the results of the FIG. 2 and shows another two examples of Poisson's ratios of 0.5 and 0.3. It also shows the repeatability over five independent renditions of the experiment.

Figure 16:
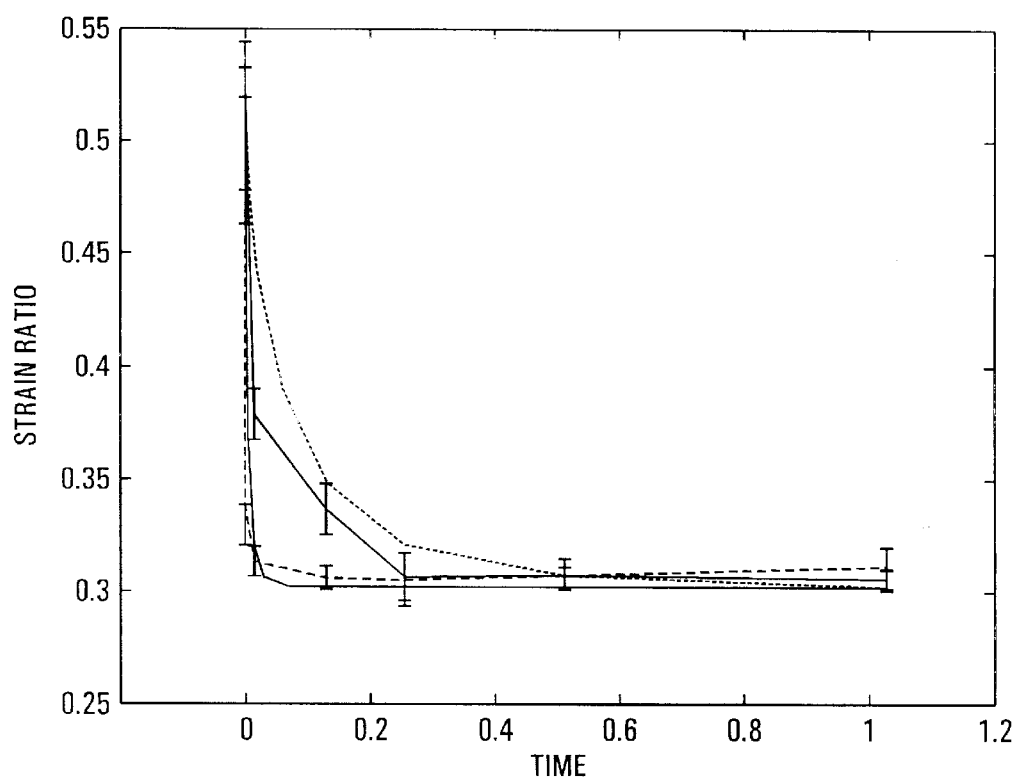
FIG. 16 is a graph of strain ratio as a function of time for various permeabilities.

FIG. 16 shows how the exponential nature of the curve can indicate the permeability of the fluid, as the definition of tg shows, assuming the aggregate modulus remains constant.

Results

1) Lateral Elastograms

Figure 4:
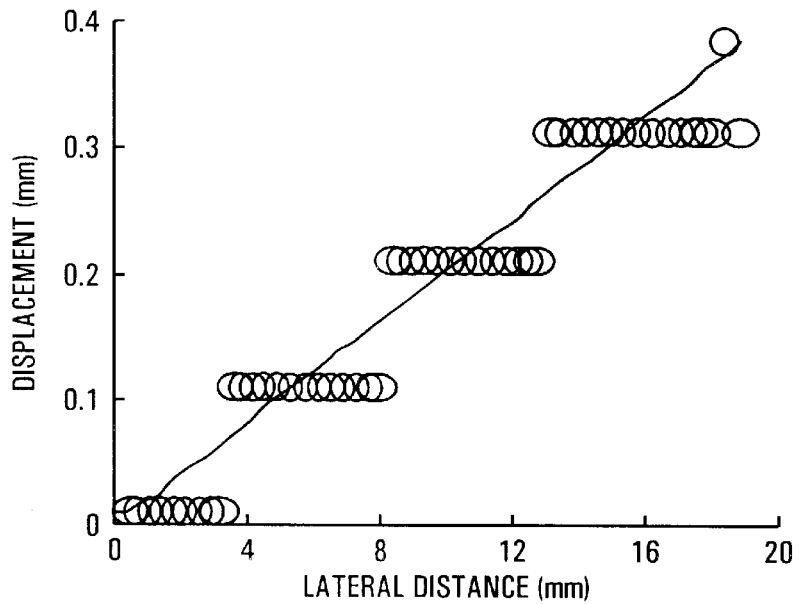
FIGS. 4 is a graph of displacement versus lateral distance.
Figure 5:
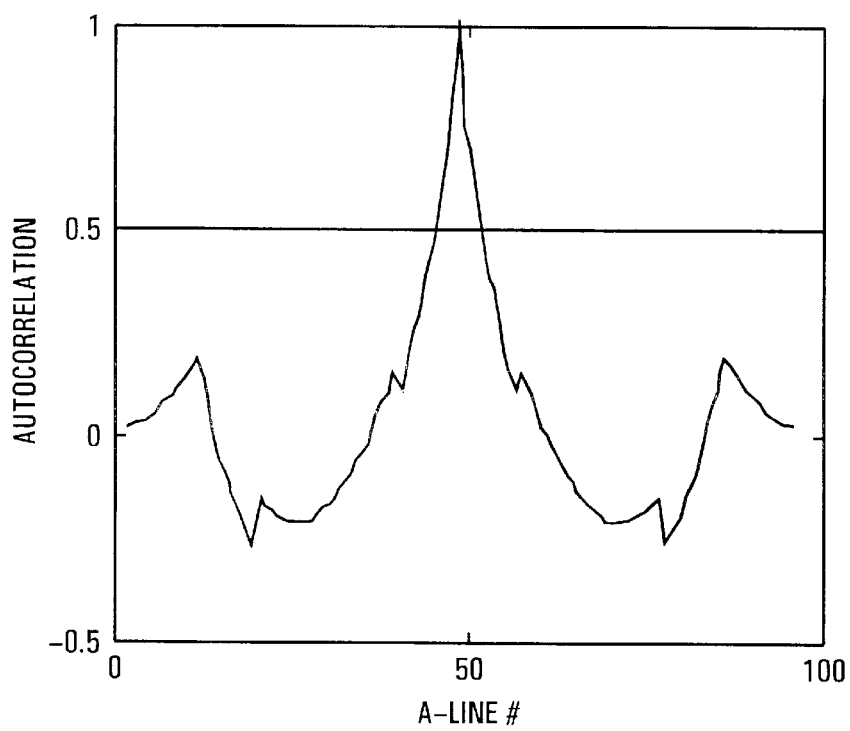
FIG. 5 is a graph of autocorrelation versus A-line number using a method of the present invention.

Table II shows the −6 dB autocorrelation widths of the residuals of the linear regression fit on the lateral displacement, obtained with beamwidths of 1, 2, 4 and 8 mm with a resulting beam overlap of 60%, 80%, 90% and 95%, respectively. The applied lateral strains (el) ranged from 0.5% to 2%, corresponding to lateral displacements of 0.2 to 0.8 mm (assuming that the lateral transducer width was 40 mm), respectively. The interpolation schemes used were 4:1, 8:1, 16:1, 32:1 and 64:1. FIGS. 4 and 5 show graphically the relationship between the width of the autocorrelation with the precision of lateral tracking using two examples of 4:1 and 32:1 interpolation, respectively, in the case of a 1 mm beamwidth and applied lateral strain of 0.5%. The data in Table II shows a substantial increase in the precision of the lateral tracking inherent in this method due to the refinement of the interpolation scheme.

TABLE II

| $\epsilon l$ | 0.5% | 1% | 1.5% | 2% | 0.5% | 1% | 1.5% | 2% |
|---|---|---|---|---|---|---|---|---|
| | beamwidth = 1 mm | | | | Beamwidth = 2 mm | | | |
| 4:1 | 2.11 | 0.66 | 1.52 | 1.68 | 0.75 | 0.89 | 0.75 | 0.86 |
| 8:1 | 1.86 | 0.51 | 0.96 | 1.44 | 0.69 | 0.72 | 0.72 | 0.66 |
| 16:1 | 0.53 | 0.38 | 0.51 | 0.45 | 0.51 | 0.72 | 0.53 | 0.64 |
| 32:1 | 0.5 | 0.38 | 0.5 | 0.5 | 0.53 | 0.78 | 0.58 | 0.66 |
| 64:1 | 0.62 | 0.38 | 0.8 | 0.5 | 0.5 | 0.77 | 0.58 | 0.66 |
| | beamwidth = 4 mm | | | | beamwidth = 8 mm | | | |
| 4:1 | 1.36 | 1.44 | 1.04 | 1.11 | 2.48 | 3.33 | 2.37 | 3.18 |
| 8:1 | 0.66 | 1.58 | 1.36 | 1.57 | 1.41 | 3.33 | 3.5 | 3.73 |
| 16:1 | 0.58 | 2 | 1.3 | 1.66 | 1.44 | 3.96 | 4.0 | 3.70 |
| 32:1 | 0.59 | 1.94 | 1.44 | 1.71 | 2.05 | 3.89 | 3.95 | 3.73 |
| 64:1 | 0.67 | 2.06 | 1.408 | 1.71 | 2.02 | 3.89 | 3.87 | 3.74 |

FIGS. 4 and 5 show the relationship between the width of the autocorrelation with the precision of lateral tracking using two examples of 4:1 and 32:1 interpolation, respectively, in the case of a 1 mm beamwidth and applied lateral strain of 0.5%. FIG. 5 discloses an increase in the precision of the lateral tracking inherent in this method due to the refinement of the interpolation scheme.

Figure 6:
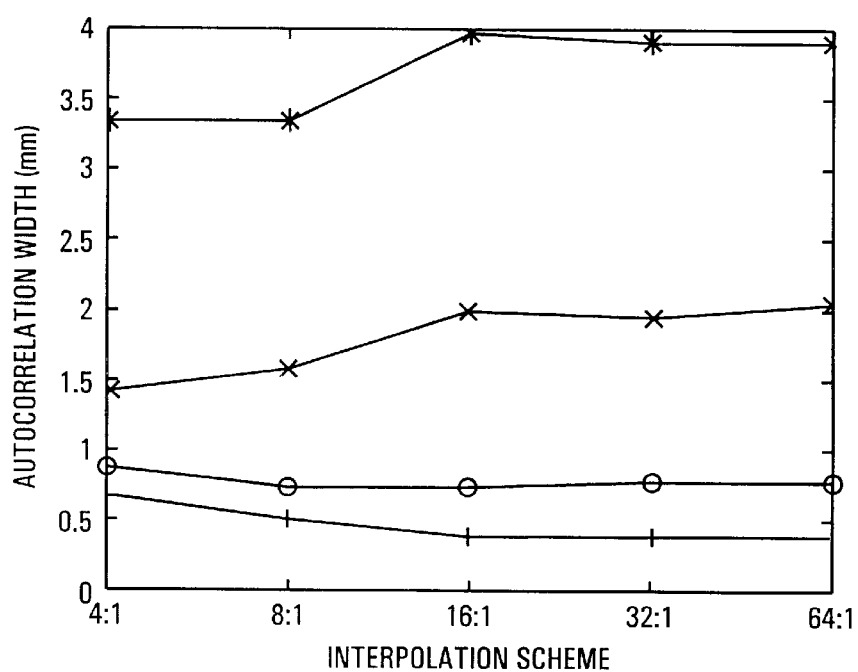
FIG. 6 is a graph of autocorrelation width versus interpolation scheme.

FIG. 6 shows graphically the results for each beamwidth case at an applied lateral strain of 1%. From the results shown in Table II one may conclude that if the appropriate interpolation scheme is used, the narrower the beamwidth the smaller the error in the lateral displacement estimation. In the area of 2D velocity measurement, there have been studies of the kernel sizes to be used when tracking laterally or axially. Bohs et al. (1995), for example, disclose that what should work best is a wide and short kernel to track the lateral motion and a tall and thin kernel to track the axial. In our case we used RF instead of envelope detected data to track the lateral displacement. Ramamurthy and Trahey (1991) found that the use of RF for 2D speckle tracking performs better than the envelope data in all cases. When interpolation is used, there is a trade-off between the beamwidth and the resulting increase in the amount of overlap. Secondly, there is a clear optimum interpolation scheme, especially in the case of higher strains.

1) Homogeneous Case (Simulation)

Figure 7A:
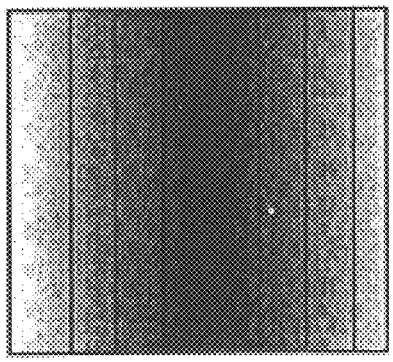
FIGS. 7a–7f are images obtained using the methods of the present invention.
Figure 7B:
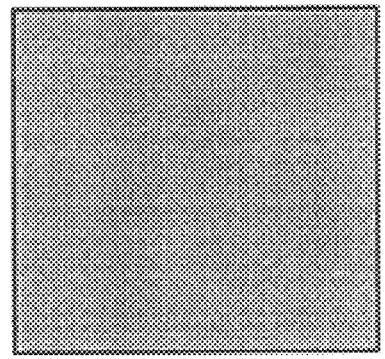
Figure 7C:
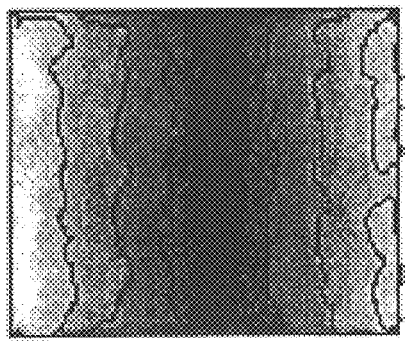
Figure 7D:
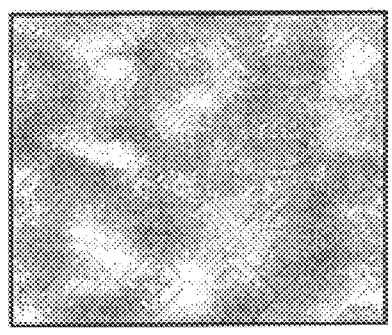

FIG. 7 shows the absolute value of the lateral displacement image (in order to show the symmetry of the lateral displacement with respect to the axis of the target) and the lateral elastogram, both for the ideal (FIGS. 7a and 7b) and the measured cases (FIGS. 7c and 7d). The high correlation between the ideal and estimated lateral elastograms is evident.

2) Homogeneous Case (Experiment)

Figure 7E:
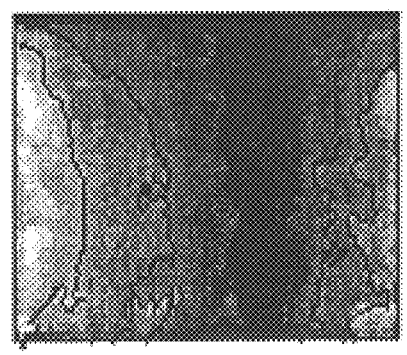
Figure 7F:
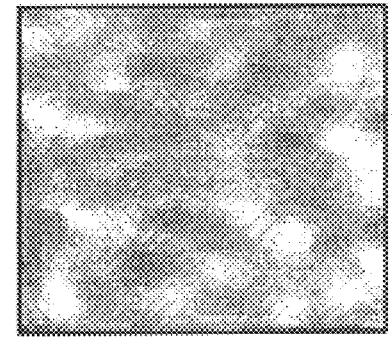

FIGS. 7e and 7f show the lateral displacement image and the lateral elastogram in the case of the homogeneous phantom after an axial compression of 1% and an axial stretching by the same amount. The isotropic displacement lines of FIGS. 7a, 7c and 7e lead to a very important observation. In FIG. 7a is shown the ideal displacement image for the case of perfect slip boundary conditions and a compression symmetrically applied around the vertical axis of the tissue. Therefore, the isometric displacement lines are perfectly parallel. FIG. 7e indicates the existence of non-perfect conditions in the experimental case. First, the compressor was not applied exactly in the middle of the tissue. Therefore, zero lateral displacement does not occur on the vertical axis of the tissue. Also, as a result of this non-uniform compression, larger maximum lateral displacement occurs on the left side of the tissue than on the right. Lastly, the isometric displacement lines are now curved, indicating the existence of non-slip conditions at the top and bottom pages of the phantom.

As a result, it can be concluded that a lateral displacement image can serve as crucial guide to the mechanical conditions, existing during an experiment. Therefore, in free-hand elastography (Bamber and Bush 1996), the lateral image can allow appropriate corrections for non-perfect in-plane compressions that may be encountered.

2) Correction of Axial Measurements For Lateral Motion

As mentioned earlier, another use for the lateral strain information is for correcting the axial measurements and thereby improving the signal-to-noise ratios in the axial and Poisson elastograms. Thus, the same lateral tracking algorithm went through a second iteration, this time using a set of post-compression RF A-lines that was computed by shifting the A-line segments that have moved laterally by the estimated lateral displacement (FIG. 3d; Chaturvedi et al. 1998). In this case, however, since the tissue was inhomogeneous, global axial stretching using the applied strain as the stretching factor cannot be optimal for both the inclusion and the background. Therefore, in this case two different corrected axial elastograms were constructed, one with a stretching factor optimal for the inclusion and one for the background. These two images were combined to a composite image where all areas were optimally axially stretched.

FIG. 8 shows axial-elastograms corresponding to an applied strain of 3% in a) the ideal case and b) without axial stretching or lateral correction, c) after axial stretching only, and d) after axial stretching and lateral correction. FIG. 8b shows how decorrelation noise corrupts the axial elastogram. The highest lateral displacement and, therefore, decorrelation occurs near the lateral sides of the phantom. FIG. 8c shows that axial stretching can partly compensate for small lateral decorrelations occurring around the axis of symmetry of the target, due to the fact that the axial and lateral deformation are coupled. By comparison of FIGS. 8c and 8d, we observe that the contrast between the inclusion and the background is increased due to axial stretching. However, axial stretching is not sufficient to correct for the large lateral displacements towards the lateral sides of the phantom. FIG. 8d shows the importance of the high precision correction of axial measurements; not only are the decorrelation artifacts eliminated but also the axial-elastogram appears to be smoother and closer to the ideal (FIG. 8a). The major remaining noise are the 'radial artifacts' in FIG. 8d, which may be due to the fact that lateral tracking is performed only on one lateral level (FIG. 3). If some tissue components move in a different direction, lateral tracking becomes noisier.

This substantial improvement is achieved through the reduction of the strain variance due to the increase of the lateral correlation coefficient. In fact, there are two levels of improvement, as shown by comparison of FIGS. 8c and d, both due to a two-level increase of the lateral correlation coefficient and, subsequently, the axial signal-to-noise ratio (Kallel et al. 1997, Varghese and Ophir 1997b). The high decorrelation noise (high intensity artifacts of FIG. 8c), where large lateral displacements occur (near the edges of the phantom), is eliminated due to lateral tracking. The subsequent increase of the axial correlation coefficient helps reduce the strain variance from the Barankin Bound to Cramer-Rao Lower Bound level (Chaturvedi et al. 1998; Kallel et al. 1997). Additionally, the lower decorrelation noise in FIG. 8c is also eliminated in FIG. 8d since the lateral correlation coefficient is further improved through this high precision lateral correction.

Figure 9:
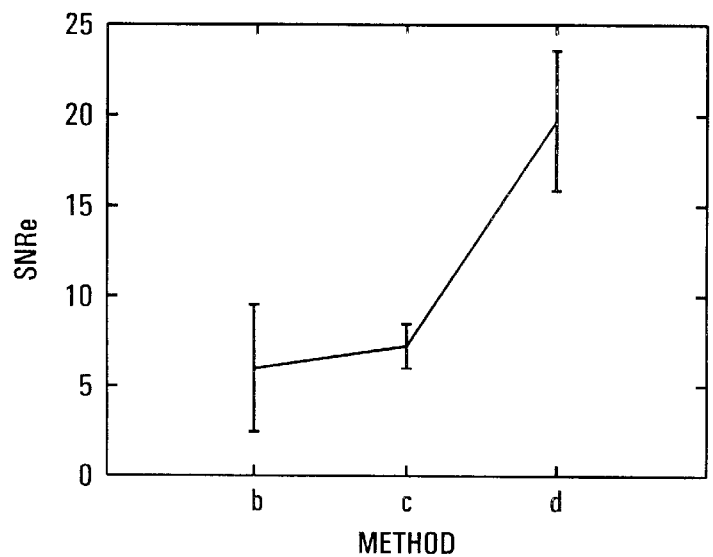
FIG. 9 is a graph of the elastographic signal to noise ratio as a function of elastrographic method used.
Figure 10:
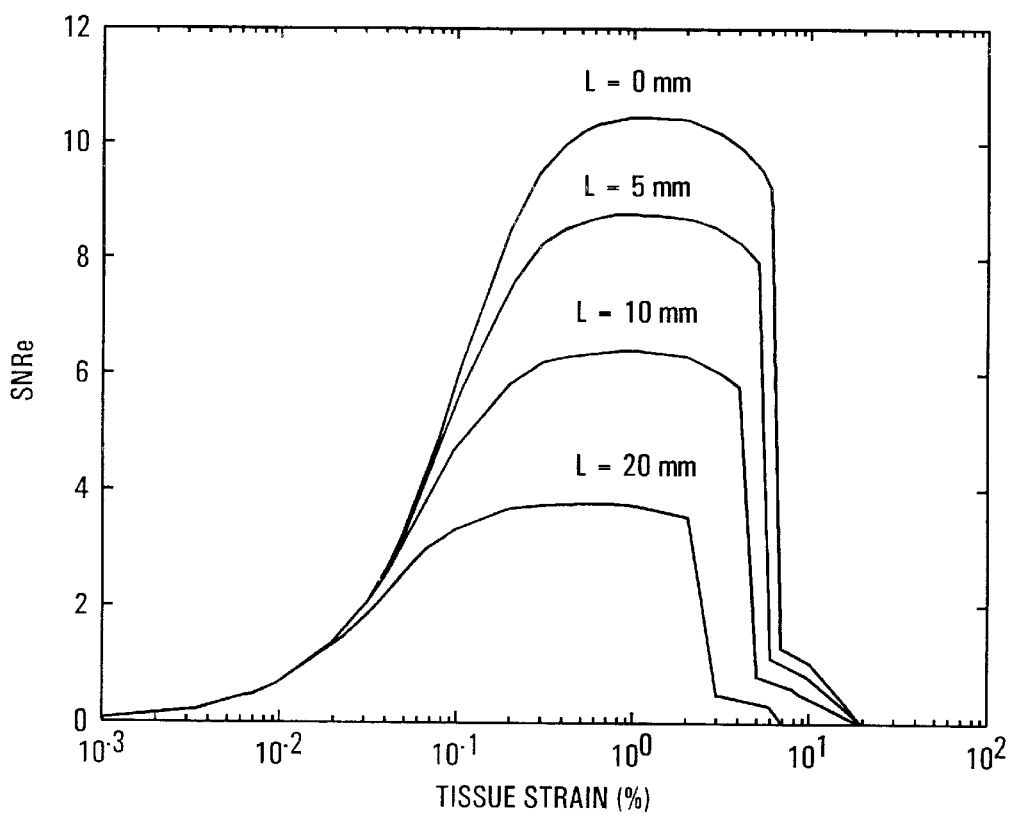
FIG. 10 is a graph of the elastographic signal to noise ration versus tissue strain for various lateral displacements.
Figure 11A:
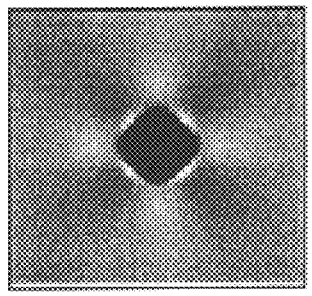
FIGS. 11a–11f are Poisson's elastograms.
Figure 11B:
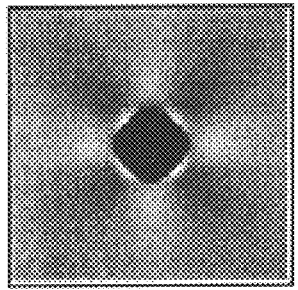
Figure 11C:
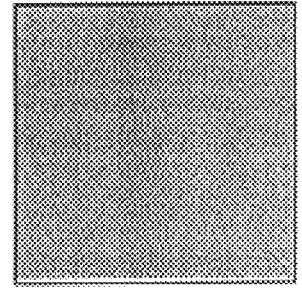
Figure 11D:
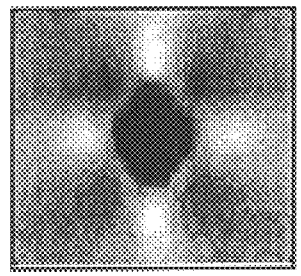
Figure 11E:
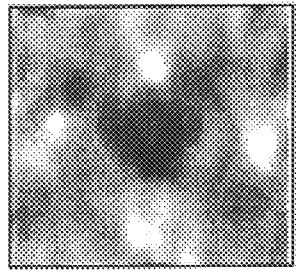
Figure 11F:
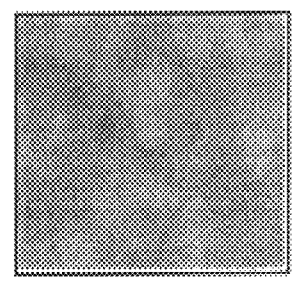
Figure 12A:
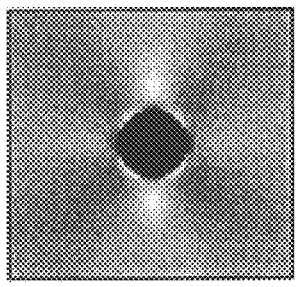
FIGS. 12a–12f are Poisson's elastograms.
Figure 12B:
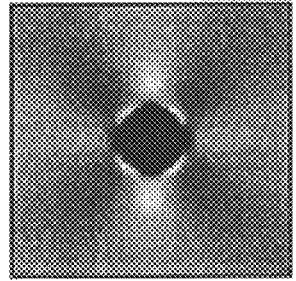
Figure 12C:
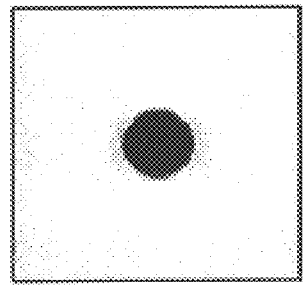
Figure 12D:
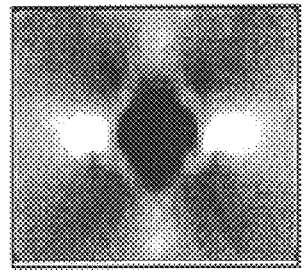
Figure 12E:
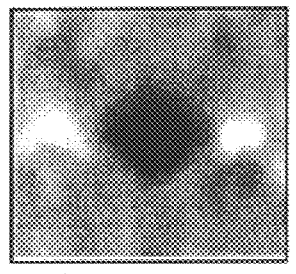
Figure 12F:
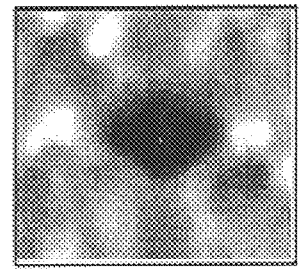

A simple observation of FIG. 8 shows how the high precision correction increases both the overall signal-to-noise ratio and the dynamic range of the axial-elastogram. FIG. 9 shows graphically the improvement in the elastographic signal-to-noise ratio ($SNR_e$)

$$SNR_e = \frac{\varepsilon_e}{\sigma_e} \tag{16}$$

where $\varepsilon_e$ and $\sigma_e$ are the estimated strain the strain standard deviation, respectively. These results are in total agreement with Kallel et al.s (1997) theoretical predictions using the strain filter, which plots the $SNR_e$ versus the estimated strain (FIG. 10). The strain filter corresponding to no corrections has a lower $SNR_e$ and a lesser upper strain range (i.e., smaller dynamic range). The zero lateral displacement case or, equivalently, the fine correction for lateral displacement at all strains, fixes both shortcomings; as is the case of this high precision lateral correction method. Lastly, the improvement described here due to the lateral correction is comparable to that achieved with lateral confinement, proposed by Kallel and Ophir (1997a). It can be concluded that lateral confinement might be redundant in the case where this method of correction for lateral motion is applied. This result shows the practicality aspect of this method and future experimental studies will be made in order assess the comparison of the two methods, i.e. the method of confinement and the correction method for lateral motion.

3) Poisson-Elastograms

FIGS. 11 and 12 show the ideal (theoretical) and estimated axial, lateral and Poisson's-elastograms for the targets without and with Poisson's-ratio contrast, respectively. In both cases, in order to create the Poisson-elastograms, the axial and lateral elastograms have been normalized and interpolated so that they have the exact same dimensions. The stress concentration artifacts in both images should cancel out during the division of Eq.1. However, due to the fact that the lateral elastograms were not corrected for axial motion, the lateral and thus the Poisson-elastograms also have a lower signal-to-noise ratio than the corrected axial-elastograms. A decrease in the lateral strain variance due to axial decorrelation can be achieved by performing a second iteration of the tracking algorithm (FIG. 1) using adaptive stretching techniques (Alam et al. 1998) on the postcompression sonogram corrected for lateral motion. It is expected that the correction for axial motion in the measurement of lateral strain should be as significant as the correction for the lateral in the axial measurement was due to an equivalent dramatic decrease in the strain variance. The lateral-elastograms and the Poisson-elastograms have a sufficiently high signal-to-noise ratio given the low Young's modulus and Poisson's ratio target contrast. In fact, from FIGS. 11e and 12e, it is obvious that the contrast-to-noise ratio has improved in the second figure in the case where there was additional Poisson's ratio contrast.

By comparing FIGS. 11d and 11e to FIGS. 12d and 12e, respectively, we find that it is impossible to ascertain from the lateral or axial-elastograms alone whether the contrast between the inclusion and the background is due to differences in the Young's moduli and/or in the Poisson's ratios between the inclusion and the background. However, when the Poisson-elastograms are computed (FIG. 11f and 12f), it is evident that in the first case there is no apparent difference in the Poisson's ratio of the inclusion and the background (so that the strain contrast can only be due to Young's modulus contrast), while in the second case there is an obvious contrast in the Poisson's ratio between the background and the inclusion. This is also demonstrated in the ideal Poisson-elastograms (FIGS. 11c and 12c).

Elastography is a method dealing with 3D mechanical problems and, therefore, a 3D treatment is necessary if optimal imaging performance is desired. Most methods used previously for lateral tracking are mainly pitch-limited, i.e., limited by the pitch of the transducer used. In this paper, we studied the lateral motion and proposed a new method for overcoming these limitations leading to a poor precision in tracking lateral speckle motion. By performing a weighted interpolation in-between beams it is possible to perform a high precision (sub-pitch) lateral tracking. This high precision is primarily due to the preservation of the precise axial phase information in the lateral interpolation.

This additional information was used in three distinct ways. First, due to the resulting high precision of its estimation, the lateral displacement was used to generate a new image displaying the lateral strain experienced by the tissue, called lateral-elastogram. From the experimental results, it can be concluded that the lateral displacement image provides us with information about the mechanical conditions existing during the experiment, such as slip or non-slip condition, position of the compressor relative to the axis of symmetry of the target and the amount of uniformity of compression. The boundary conditions are crucial parameters in designing an elastographic experiment and they may be indicated by the lateral (displacement and/or strain) image. In addition, in free-hand elastography, the lateral image can provide essential correction factors to the relatively poorly controlled compressor motion. Acquiring a high precision lateral displacement image may also be important in other modalities as well, such as transverse blood flow imaging that is not limited by the Doppler angle.

Second, the lateral strain information was used to shift accordingly the laterally displaced A-lines and to compute a corrected axial elastogram that suffers from much less decorrelation errors than an uncorrected one. An important finding of this work was that there are two kinds of decorrelation noise that are corrected using a finer correction method. One advantage is the increase of the signal-to-noise ratio at the higher strains. The most important advantage, however, is the improvement of the signal-to-noise ratio at all strains due to the ability of the algorithm to correct for all lateral motions, whether fine or large. This leads to a significant increase in the overall signal-to-noise ratio of the corrected axial-elastogram, both near the edge of the elastogram and elsewhere. These results are comparable to the results obtained after lateral confinement, but more thorough studies should be made to investigate if this high precision correction method is sufficient even when lateral confinement is not used.

In the same way, the axial information can be used to correct the lateral strain estimation. However, this method requires the precision of an adaptive stretching algorithm that corrects for the axial strain with higher precision than the global stretching. This will be considered in future studies in order to improve the signal-to-noise ratio of the lateral-elastogram, and thus of the Poisson-elastogram as well.

The same concept of fine tracking in-between beams can be extended in principle to elevational tracking as well if a 1.5 or 2D array becomes available. This allows a two-dimensional correction of the axial estimation and/or the generation of three-dimensional elastograms, thereby allowing the full description of the entire 3D mechanical problem.

Finally, a second new image was introduced, called Poisson-elastogram, that depicts the Poisson's ratio distribution in the target. We were able to show that if there is a strain contrast between an inclusion and the background, the Poisson-elastogram is able to show whether this strain contrast is due to a Poisson's ratio contrast or an elastic modulus contrast. The Poisson-elastograms may have interesting applications in assessing the degree of water content in tissues. The Poisson-elastogram or a time-sequence of Poisson-elastograms may be used for quantitative assessment of fluid transport in edema and other poroelasticity problems. Another interesting property of the Poisson-elastogram is that it forms an image that is free from mechanical artifacts (Ophir et al. 1996). Also, the knowledge of both lateral strain and the Poisson's ratio in addition to the axial strain is in general necessary for reconstruction algorithms (Skovoroda 1995; Sumi 1995; Kallel 1996) so that the final modulus image could become more accurate if the lateral and Poisson-elastograms are first computed.

The present invention may also be used to estimate shearing strain or shear strain in the target body. Shearing strain ($\epsilon_{xy}$) can also be estimated from the axial and lateral/elevational displacement information. Shearing strain is defined by $$\varepsilon_{xy} = \frac{1}{2}\left[\frac{\partial u}{\partial y} + \frac{\partial v}{\partial x}\right] \quad (17)$$

where u and v are the axial (x-direction) and lateral (y-direction) displacements, as part of the strain tensor given by $$E = \begin{bmatrix} \varepsilon_x & \varepsilon_{xy} & \varepsilon_{zx} \\ \varepsilon_{yx} & \varepsilon_y & \varepsilon_{yx} \\ \varepsilon_{zx} & \varepsilon_y & \varepsilon_z \end{bmatrix}, \quad (18)$$

where $$\varepsilon_{ij} = \frac{1}{2}\left(\frac{\partial u_i}{\partial X_j} + \frac{\partial u_j}{\partial X_i}\right) \quad (19)$$

and $\epsilon_{xy}$, $\epsilon_{yz}$, and $\epsilon_{zx}$ are the small changes in right angles whose sides were initially parallel to the x- and y-, y- and z-, z- and x-axes, respectively (note $\epsilon_{ii}=\epsilon_i$). The use of axial and lateral displacements in the present invention is depicted in FIG. 1G.

The foregoing disclosure and description of the invention are illustrative and explanatory. Various changes in the size, shape, and materials, as well as in the details of the illustrative embodiments may be made without departing from the spirit of the invention.

What is claimed is:

1. A method for finding a match between echo sequences in each of two adjacent overlapping beams comprising:
   a. acoustically coupling at least two spaced ultrasound sources to a target body, said sources spaced apart a distance d, such that said beams overlap;
   b. emitting a first pulse of ultrasound energy along the axis of each beam and into the target body;
   c. recording the arrival time of the first echo sequence having at least one echo segment arriving in response to said first pulse of ultrasound energy within each beam;
   d. emitting a next pulse of ultrasound energy along each beam axis;
   e. recording the arrival time of a next echo sequence for each beam emitted in step (d);
   f. storing the previously recorded data in a retrievable medium; and
   g. finding a match of at least one first echo sequence of a beam emitted in step (a) to next said echo sequence of a beam emitted in step (d).

2. The method of claim 1 further comprising:
   a. estimating the transverse displacements from the locations of one or more transverse matches of step (g) of claim 1; and
   b. estimating the slope of the transverse displacement recorded in the prior step in any direction to estimate the transverse strain.

3. The method of claim 2, further comprising:
   a. estimating the transverse strain; and
   b. estimating the ratio between the transverse and axial strains.

4. The method of claim 1 wherein said finding comprises:
   a. cross correlating at least one of said first echo sequences to at least one of said next echo sequences;
   b. estimating the location of a peak of the cross correlation function by interpolating the cross correlation function; and
   c. interpolating between the cross correlation values of step (b) to determine the location of a peak in the transverse direction, which designates the transverse displacement for each echo sequence.

5. The method of claim 4, further comprising:
   a. estimating the axial displacement; and
   b. estimating shear strain in said target body.

6. The method of claim 5, further comprising:
   a. estimating the transverse strain;
   b. storing data selected from the group of the estimated transverse strain, estimated shear strain or estimated transverse displacement;
   c. repeating the preceding two steps for different regions of the target body; and
   d. displaying the stored data.

7. The method of claim 5, further comprising:
   a. estimating the strain ratio;
   b. storing the estimated strain ratio;
   c. repeating the preceding two steps for different regions of the body;
   d. displaying the stored strain ratio estimate.

8. The method of claim 1, further comprising:
   a. constructing echo sequences comprising the transverse matches determined in step (g) of claim 1;
   b. estimating the axial displacement and strains of said echo sequences;
   c. correcting at least one of said echo sequences recorded in claim 1 for the axial or transverse displacements and strains from the echo sequence of the preceding step; and
   d. repeating steps a-c to estimate corrected axial and transverse displacements and strains.

9. The method of claim 1 wherein further comprising displacing a surface of the body after step (c) and before step (d) of claim 1.

10. The method of claim 9, further comprising correcting at least one said echo sequence from claim 1, said correcting performed after step (f) and before step (g) of claim 1.

11. The method of claim 9, wherein said displacing is compressing.

12. A method for finding a match between echo sequences in each of two adjacent overlapping beams comprising:
   a. acoustically coupling at least two spaced ultrasound sources to a target body, said sources spaced apart a distance d, such that said beams overlap;
   b. emitting a first pulse of ultrasound energy along the axis of each beam and into the target body;
   c. recording the arrival time of the first echo sequence having at least one echo segment arriving in response to said first pulse of ultrasound energy within each beam;
   d. compressing the surface of the body;
   e. emitting a next pulse of ultrasound energy along each beam axis;
   f. recording the arrival time of a next echo sequence for each beam emitted in step (d);
   g. storing the previously recorded data in a retrievable medium; and
   h. finding a match of at least one first echo sequence of a beam emitted in step (a) to next said echo sequence of a beam emitted in step (d).

13. The method of claim 12 further comprising:
   a. acquiring at least two additional echo sequences at a preselected time interval; and b. estimating the strain ratio from the precompressed echo sequence and at least two subsequent echo sequences.

14. The method of claim 12 further comprising correcting at least one said echo sequence from claim 1, said correcting performed after step g and before step h of claim 12.

15. The method of claim 12 further comprising
   a. storing the strain ratios estimated in step (b) of claim 13;
   b. repeating steps (a) through (b) of claim 13 and the preceding step for different regions in the target body; and
   c. displaying the stored strain ratio estimate.

16. The method of claim 12, further comprising:
   a. estimating the transverse strain;
   b. storing data selected from the group of the estimated transverse strain, estimated shear strain or estimated transverse displacement;
   c. repeating the preceding two steps for different regions of the target body; and
   d. displaying stored data.

17. A method for finding the location of a peak of a cross correlation function comprising:
   a. acoustically coupling at least two spaced ultrasound sources to a target body, said sources spaced apart a distance d, such that said beams overlap;
   b. emitting a first pulse of ultrasound energy along the axis of each beam and into the target body;
   c. recording the arrival time of the first echo sequence having at least one echo segment arriving in response to said first pulse of ultrasound energy within each beam;
   d. emitting a next pulse of ultrasound energy along each beam axis;
   e. recording the arrival time of a next echo sequence for each beam emitted in step (d);
   f. storing the previously recorded data in a retrievable medium;
   g. cross correlating at least one of said first echo sequence to its transverse match of said next echo sequence;
   h. estimating the location of a peak of the cross correlation function by interpolating the cross correlation function; and
   i. interpolating between the cross correlation values of the preceding step to locate a peak in the transverse direction.

18. The method of claim 17, further comprising:
   a. constructing echo sequences comprising the transverse matches determined in step (g) of claim 17;
   b. estimating the axial displacement and strains of said echo sequences;
   c. correcting at least one of said echo sequences recorded in claim 17 for the axial displacements and strains from the echo sequence of the preceding step; and
   d. repeating steps a-c to estimate corrected axial and transverse displacements and strains.

19. The method of claim 18 further comprising estimating the ratio between any two strains estimated in step (d) of claim 18.

20. The method of claim 19 further comprising
   a. storing the strain ratios estimated in claim 19;
   b. repeating the steps of claim 19; and
   c. displaying the stored strain estimate.

21. The method of claim 17 further comprising:
   a. estimating the transverse displacements from the locations of one or more transverse matches of step (g) of claim 17; and
   b. estimating the slope of the transverse displacement recorded in the prior step in any direction to estimate the transverse strain.

22. The method of claim 21, further comprising:
   a. estimating the transverse strain;
   b. storing data selected from the group of the estimated transverse strain, estimated shear strain or estimated transverse displacement;
   c. repeating the preceding two steps for different regions of the target body; and
   d. displaying the stored data.

23. A method for finding a match between two echo sequences comprising:
   a. acoustically coupling at least two spaced ultrasound sources to a target body, said sources spaced apart a distance d, such that said beams overlap;
   b. emitting a first pulse of ultrasound energy along the axis of each beam and into the target body;
   c. recording the arrival time of the first echo sequence having at least one echo segment arriving in response to said first pulse of ultrasound energy within each beam;
   d. emitting a next pulse of ultrasound energy along each beam axis;
   e. recording the arrival time of a next echo sequence for each beam emitted in step (d);
   f. storing the previously recorded data in a retrievable medium;
   g. interpolating between at least two transversely spaced echo sequences to produce at least one interpolated echo sequence; and
   h. finding a match of at least one interpolated echo sequence with one other echo sequence.

24. The method of claim 23 further comprising:
   a. estimating the displacements from the locations of one or more transverse matches of step (g) of claim 23; and
   b. estimating the slope of the transverse displacement recorded in the prior step in any direction to estimate the transverse strain.

25. The method of claim 24, further comprising:
   a. estimating the transverse strain;
   b. storing data selected from the group of the estimated transverse strain, estimated shear strain or estimated transverse displacement;
   c. repeating the preceding two steps for different regions of the target body; and
   d. displaying the stored data.

26. The method of claim 23, further comprising:
   a. estimating the strain ratio;
   b. storing the estimated strain ratio in the form of strain ratio data;
   c. repeating the preceding two steps for different regions of the body;
   d. displaying the stored data.

27. The method of claim 23 wherein further comprising displacing a surface of the body after step (c) and before step (d) of claim 23.

* * * * *

UNITED STATES PATENT AND TRADEMARK OFFICE
CERTIFICATE OF CORRECTION

PATENT NO. : 6,270,459 B1  Page 1 of 3
DATED : August 7, 2001
INVENTOR(S) : Konofagou et al.

It is certified that error appears in the above-identified patent and that said Letters Patent is hereby corrected as shown below:

Title page,
Item [56], References Cited, delete "Sarvazyon, et al.", and insert -- Sarvazyan, et al. --

Drawings,
Figure 1A, Sheet 1 of 15 delete.

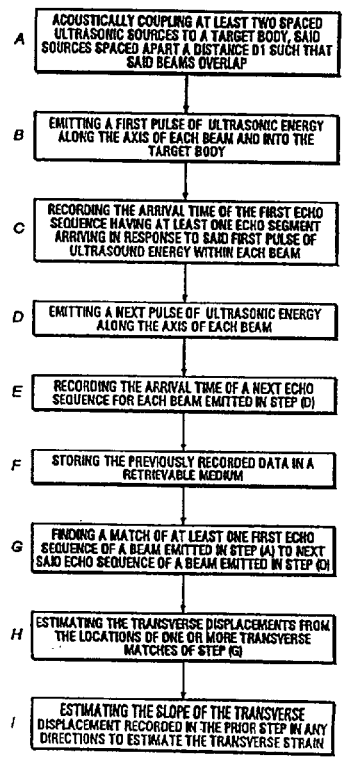

FIG. 1A

UNITED STATES PATENT AND TRADEMARK OFFICE
CERTIFICATE OF CORRECTION

PATENT NO.    : 6,270,459 B1
DATED         : August 7, 2001
INVENTOR(S)   : Konofagou et al.

It is certified that error appears in the above-identified patent and that said Letters Patent is hereby corrected as shown below:

<u>Drawings,</u>
Figure 1A, 1/15, insert.
--

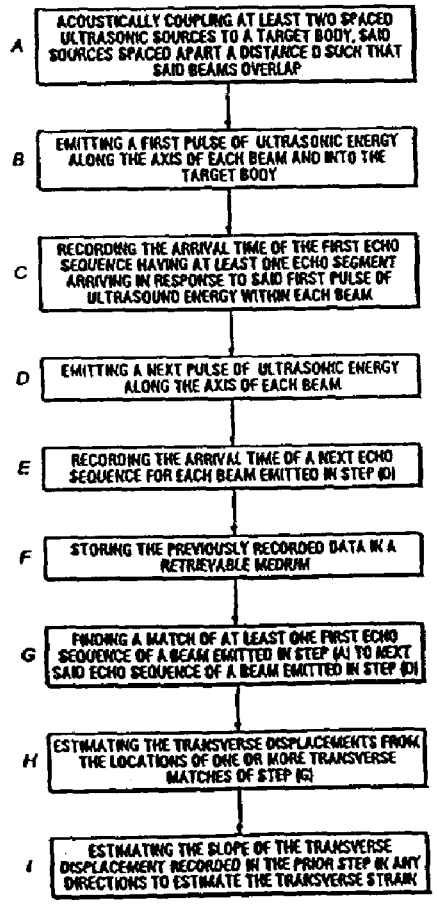

FIG. 1A

--

UNITED STATES PATENT AND TRADEMARK OFFICE
CERTIFICATE OF CORRECTION

PATENT NO. : 6,270,459 B1
DATED : August 7, 2001
INVENTOR(S) : Konofagou et al.

It is certified that error appears in the above-identified patent and that said Letters Patent is hereby corrected as shown below:

Column 2,
Line 41, (26), delete "Kaliel", and insert -- Kallel --.
Line 49, (28), delete "Kaliel", and insert -- Kallel -- .

Column 7,
Line 3, (26), delete "FIG. 1E is a block diagram of the ratio estimating and", and insert -- FIG. 1E is a block diagram of the strain ratio estimating and --.
Line 14, delete "FIGS. 4 is a graph of displacement versus lateral distance", and insert -- FIG. 4 is a graph of lateral displacement versus lateral distance --.
Line 28, delete "ration versus tissue strain for various lateral displacements", and insert -- ratio versus tissue strain for various lateral displacements --.
Line 29, delete "FIGS. l$a$-11$f$ are Poisson's elastrograms", and insert
--FIGS. 1 l$a$-11$f$ are Poisson's ratio elastrograms --.
Line 30, delete "FIGS. 12$a$-12$f$ are Poisson's elastograms" and insert -- FIGS. 12$a$-12$f$ are Poisson's ratio elastrograms --.

Column 16,
Line 4, delete "Hibbift, Karlsson & Sorenson, Inc. of Pawtucket, RI. In this", and insert -- "Hibbit, Karlsson & Sorenson, Inc. of Pawtucket, RI. In this" --.

Column 18,
Line 56, delete "with Kallel et al.s (1997) theoretical predictions using the", and insert -- "with Kallel et al.'s (1997) theoretical predictions using the" --.

Signed and Sealed this

Third Day of December, 2002

JAMES E. ROGAN
*Director of the United States Patent and Trademark Office*

UNITED STATES PATENT AND TRADEMARK OFFICE
CERTIFICATE OF CORRECTION

PATENT NO. : 6,270,459 B1
DATED : August 7, 2001
INVENTOR(S) : Elisa Konofagou and Jonathan Ophir It is certified that error appears in the above-identified patent and that said Letters Patent is hereby corrected as shown below:

Column 1,
Line 12, insert -- GOVERNMENT RIGHTS
This invention was made with United States Government support under Grant No. PO1-CA64597, awarded by the National Cancer Institute. The United States Governement has certain rights in the invention. --

Signed and Sealed this

Ninth Day of August, 2005

JON W. DUDAS
*Director of the United States Patent and Trademark Office*